(12) United States Patent
Popplewell et al.

(10) Patent No.: US 7,105,064 B2
(45) Date of Patent: Sep. 12, 2006

(54) PARTICULATE FRAGRANCE DEPOSITION ON SURFACES AND MALODOUR ELIMINATION FROM SURFACES

(75) Inventors: Lewis Michael Popplewell, Morganville, NJ (US); Yueqian Zhen, Tredyffrin, PA (US); Cory Michael Bryant, Washington, DC (US); Johan Gerwin Lodewijk Pluyter, Middletown, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 323 days.

(21) Appl. No.: 10/718,368

(22) Filed: Nov. 20, 2003

(65) Prior Publication Data

US 2005/0113267 A1    May 26, 2005

(51) Int. Cl.
  *B08B 3/04* (2006.01)
(52) U.S. Cl. .............................. 134/42; 510/438; 512/4
(58) Field of Classification Search ...................... None
  See application file for complete search history.

(56) References Cited

U.S. PATENT DOCUMENTS

| | | | |
|---|---|---|---|
| 2,800,457 A | 7/1957 | Green et al. |
| 3,041,288 A | 6/1962 | Anthony |
| 3,415,758 A | 12/1968 | Powell et al. |
| 3,505,432 A | 4/1970 | Neuwald |
| 3,516,846 A | 6/1970 | Matson |
| 3,516,941 A | 6/1970 | Matson |
| 3,686,025 A | 8/1972 | Morton |
| 3,861,870 A | 1/1975 | Edwards et al. |
| 3,870,542 A | 3/1975 | Ida et al. |
| 4,081,384 A | 3/1978 | Pracht |
| 4,082,223 A | 4/1978 | Nozawa |
| 4,124,521 A | 11/1978 | Jedzinak |
| 4,145,184 A | 3/1979 | Brain et al. |
| 4,209,417 A | 6/1980 | Whyte |
| 4,234,627 A | 11/1980 | Schilling |
| 4,247,498 A | 1/1981 | Castro |
| 4,318,818 A | 3/1982 | Letton et al. |
| 4,387,090 A | 6/1983 | Bolich, Jr. |
| 4,395,541 A | 7/1983 | Jacquet et al. |
| 4,402,856 A | 9/1983 | Schnoring et al. |
| 4,424,134 A | 1/1984 | Sissin et al. |
| 4,428,869 A | 1/1984 | Munteanu et al. |
| 4,446,032 A | 5/1984 | Munteanu et al. |
| 4,446,042 A | 5/1984 | Leslie |
| 4,514,461 A | 4/1985 | Woo |
| 4,515,705 A | 5/1985 | Moeddel |
| 4,521,541 A | 6/1985 | Rutherford et al. |
| 4,534,891 A | 8/1985 | Boden et al. |
| 4,537,706 A | 8/1985 | Severson, Jr. |
| 4,537,707 A | 8/1985 | Severson, Jr. |
| 4,539,135 A | 9/1985 | Ramachandran et al. |
| 4,550,862 A | 11/1985 | Barker et al. |

(Continued)

OTHER PUBLICATIONS

Lee, et al, Microencapsulation of Fragrant Oil via in situ polymerization of pH and melamine-formaldehyde molar ratio, J.Microencapsulation, 2002, vol. 19, No. 5, pp. 559-569.

(Continued)

*Primary Examiner*—John R. Hardee
(74) *Attorney, Agent, or Firm*—Elizabeth M Quirk

(57) ABSTRACT

Described is a process for imparting a fragrance to, and/or eliminating a malodour from solid or semi-solid surfaces through the use of polymeric particles. The polymeric particles have infrastructures composed of ethylene-vinyl copolymers, polymethyl methacrylate, polystyrene and/or ethylcellulose. Also described are aqueous treatment compositions for use in such processes.

3 Claims, 13 Drawing Sheets

U.S. PATENT DOCUMENTS

| | | |
|---|---|---|
| 4,561,998 A | 12/1985 | Wertz et al. |
| 4,597,898 A | 7/1986 | Vander Meer |
| 4,597,962 A | 7/1986 | Grollier et al. |
| 4,673,568 A | 6/1987 | Grollier et al. |
| 4,681,806 A | 7/1987 | Matkan et al. |
| 4,705,681 A | 11/1987 | Maes et al. |
| 4,714,562 A | 12/1987 | Roselle et al. |
| 4,731,243 A | 3/1988 | Lindauer et al. |
| 4,767,547 A | 8/1988 | Straathof et al. |
| 4,819,835 A | 4/1989 | Tasaki |
| 4,828,542 A | 5/1989 | Hermann |
| 4,830,855 A | 5/1989 | Stewart |
| 4,917,920 A | 4/1990 | Ono et al. |
| 4,961,871 A | 10/1990 | Michael |
| 4,968,451 A | 11/1990 | Scheibel et al. |
| 4,973,422 A | 11/1990 | Schmidt |
| 5,066,419 A | 11/1991 | Walley et al. |
| 5,085,857 A | 2/1992 | Reid et al. |
| 5,112,688 A | 5/1992 | Michael |
| 5,137,646 A | 8/1992 | Schmidt et al. |
| 5,154,842 A | 10/1992 | Walley et al. |
| 5,160,655 A | 11/1992 | Donker et al. |
| 5,169,552 A | 12/1992 | Wise |
| 5,188,753 A | 2/1993 | Schmidt et al. |
| 5,194,639 A | 3/1993 | Connor et al. |
| 5,232,769 A | 8/1993 | Yamato et al. |
| 5,237,035 A | 8/1993 | O'Lenick, Jr. et al. |
| 5,275,755 A | 1/1994 | Sebag et al. |
| 5,288,417 A | 2/1994 | Bauer et al. |
| 5,288,431 A | 2/1994 | Huber et al. |
| 5,403,499 A | 4/1995 | Kiefer et al. |
| 5,411,671 A | 5/1995 | Bauer et al. |
| 5,458,809 A | 10/1995 | Fredj et al. |
| 5,458,810 A | 10/1995 | Fredj et al. |
| 5,460,752 A | 10/1995 | Fredj et al. |
| 5,466,802 A | 11/1995 | Panandiker et al. |
| 5,470,507 A | 11/1995 | Fredj et al. |
| 5,500,138 A | 3/1996 | Bacon et al. |
| 5,534,197 A | 7/1996 | Scheibel et al. |
| 5,540,853 A | 7/1996 | Trinh et al. |
| 5,545,340 A | 8/1996 | Wahl et al. |
| 5,545,350 A | 8/1996 | Baker et al. |
| 5,559,261 A | 9/1996 | Sivik |
| 5,562,849 A | 10/1996 | Wahl et al. |
| 5,565,145 A | 10/1996 | Watson et al. |
| 5,574,179 A | 11/1996 | Wahl et al. |
| 5,581,005 A | 12/1996 | Perkins |
| 5,597,936 A | 1/1997 | Perkins et al. |
| 5,618,523 A | 4/1997 | Zysman et al. |
| 5,661,118 A | 8/1997 | Cauwet et al. |
| 5,665,822 A | 9/1997 | Bitler et al. |
| 5,674,832 A | 10/1997 | Keys |
| 5,679,630 A | 10/1997 | Baeck et al. |
| 5,703,030 A | 12/1997 | Perkins et al. |
| 5,703,034 A | 12/1997 | Offschack et al. |
| 5,705,464 A | 1/1998 | Scheper et al. |
| 5,726,144 A | 3/1998 | Dewez et al. |
| 5,731,278 A | 3/1998 | Nair et al. |
| 5,756,436 A | 5/1998 | Royce et al. |
| 5,759,990 A | 6/1998 | Wahl et al. |
| 5,776,443 A | 7/1998 | Vinski et al. |
| 5,776,883 A | 7/1998 | Vasudevan |
| 5,783,302 A | 7/1998 | Bitler et al. |
| 5,837,661 A | 11/1998 | Evans et al. |
| 5,849,313 A | 12/1998 | Fost et al. |
| 5,877,145 A | 3/1999 | Wahl et al. |
| 5,902,781 A | 5/1999 | Painter |
| 5,914,307 A | 6/1999 | DeNome et al. |
| 5,916,862 A | 6/1999 | Morelli et al. |
| 5,929,022 A | 7/1999 | Velazquez |
| 5,932,203 A | 8/1999 | Coffindaffer et al. |
| 5,935,561 A | 8/1999 | Inman et al. |
| 5,939,373 A | 8/1999 | Haeggberg et al. |
| 5,962,386 A | 10/1999 | Scheper et al. |
| 5,968,286 A | 10/1999 | Crudele et al. |
| 5,968,404 A | 10/1999 | Trinh et al. |
| 5,968,881 A | 10/1999 | Haeggberg et al. |
| 5,990,065 A | 11/1999 | Vinson et al. |
| 6,001,343 A | 12/1999 | Trinh et al. |
| 6,017,871 A | 1/2000 | Baeck et al. |
| 6,020,294 A | 2/2000 | Getty et al. |
| 6,024,943 A | 2/2000 | Ness et al. |
| 6,057,404 A | 5/2000 | Utecht et al. |
| 6,069,122 A | 5/2000 | Vinson et al. |
| 6,071,569 A | 6/2000 | Stambaugh |
| 6,106,875 A | 8/2000 | Soper et al. |
| 6,113,935 A | 9/2000 | Rodson et al. |
| 6,133,226 A | 10/2000 | Knowlton et al. |
| 6,143,707 A | 11/2000 | Trinh et al. |
| 6,146,621 A | 11/2000 | Trinh et al. |
| 6,162,423 A | 12/2000 | Sebag et al. |
| 6,180,594 B1 | 1/2001 | Fender et al. |
| 6,190,678 B1 | 2/2001 | Hasenoehrl et al. |
| 6,194,375 B1 | 2/2001 | Ness et al. |
| 6,200,554 B1 | 3/2001 | Yeoh et al. |
| 6,221,826 B1 | 4/2001 | Surutzidis et al. |
| 6,248,315 B1 | 6/2001 | Young et al. |
| 6,255,367 B1 | 7/2001 | Bitler et al. |
| 6,261,483 B1 | 7/2001 | Frank et al. |
| 6,268,431 B1 | 7/2001 | Snyder et al. |
| 6,297,203 B1 | 10/2001 | Guskey et al. |
| 6,297,210 B1 | 10/2001 | Hsu et al. |
| 6,329,057 B1 | 12/2001 | Dungworth et al. |
| 6,335,315 B1 | 1/2002 | Trinh et al. |
| 6,355,234 B1 | 3/2002 | Birtwistle et al. |
| 6,413,548 B1 | 7/2002 | Hamer et al. |
| 6,436,383 B1 | 8/2002 | Murray |
| 6,451,065 B1 | 9/2002 | Trinh et al. |
| 6,458,754 B1 | 10/2002 | Velaquez et al. |
| 6,492,462 B1 | 12/2002 | Bitler et al. |
| 6,495,058 B1 | 12/2002 | Frankenbach et al. |
| 6,509,034 B1 | 1/2003 | Calanchi et al. |
| 6,514,487 B1 | 2/2003 | Barr |
| 6,514,489 B1 | 2/2003 | Shacknai et al. |
| 6,514,504 B1 | 2/2003 | Yen et al. |
| 6,514,918 B1 | 2/2003 | Librizzi |
| 6,514,923 B1 | 2/2003 | Cheung et al. |
| 6,517,588 B1 | 2/2003 | Hopkinson |
| 6,521,589 B1 | 2/2003 | Demeyere et al. |
| 6,524,494 B1 | 2/2003 | Hart et al. |
| 6,528,046 B1 | 3/2003 | Schmenger et al. |
| 6,531,113 B1 | 3/2003 | Mougin et al. |
| 6,531,437 B1 | 3/2003 | Ryan et al. |
| 6,540,989 B1 | 4/2003 | Janchitraponvej |
| 6,544,535 B1 | 4/2003 | Sakurai et al. |
| 6,551,604 B1 | 4/2003 | Beck et al. |
| 6,555,098 B1 | 4/2003 | Murphy et al. |
| 6,569,826 B1 | 5/2003 | Chiaradonna et al. |
| 6,592,813 B1 | 7/2003 | Fox et al. |
| 6,620,777 B1 | 9/2003 | Heibel et al. |
| 6,645,479 B1 | 11/2003 | Shefer et al. |
| 6,849,591 B1 * | 2/2005 | Boeckh et al. ............... 510/475 |
| 2002/0016269 A1 | 2/2002 | Noda et al. |
| 2003/0005522 A1 | 1/2003 | Trinh et al. |
| 2003/0013632 A1 | 1/2003 | Santos et al. |
| 2003/0069164 A1 | 4/2003 | Levinson |
| 2003/0092600 A1 | 5/2003 | Shepherd, Jr. |
| 2003/0119713 A1 | 6/2003 | Heltovics et al. |
| 2003/0125222 A1 | 7/2003 | Jahns et al. |
| 2003/0158072 A1 | 8/2003 | Goodson et al. |
| 2003/0171246 A1 | 9/2003 | Boeckh et al. |
| 2003/0199412 A1 | 10/2003 | Gupta et al. |
| 2003/0215417 A1 | 11/2003 | Uchiyama et al. |
| 2004/0071742 A1 | 4/2004 | Popplewell et al. |

| | | |
|---|---|---|
| 2004/0071746 A1 | 4/2004 | Popplewell et al. |
| 2004/0072719 A1 | 4/2004 | Bennett et al. |
| 2004/0072720 A1 | 4/2004 | Brain et al. |
| 2005/0003996 A1 | 1/2005 | Santos et al. |
| 2005/0043209 A1 | 2/2005 | Schmiedel et al. |

OTHER PUBLICATIONS

Lochhead, et al, Encyclopedia of Polymers and Thickeners for Cosmetics, Cosmetics & Toiletries, vol. 108, May 1993, pp. 95-138.

Kashikl, On a New Type of Flocculant, Ind.Eng.Chem.Fundam., 1986, 25, pp. 120-125.

Wurzburg, et al, Modified Starches:Properties and Uses, CRC Press, Inc., Chapter 3-Cross-Linked Starches, Chapter 8-Cationic Starches and Chapter 10-Grafted Starches.

Barton, CRC Handbook of Polymer-Liquid Interaction Parameters and Solubility Parameters, CRC Press, Part I, Introduction.

Gmehling, et al, Vapor-Liquid Equilibria by UNIFAC Group Contribution.Revision and Extension.2, Ind.Eng.Chem.Process Des. Dev., 1982, 21, pp. 118-127.

Jacobson, Molecular Modeling Studies of Polymeric Transdermal Adhesives:Structure and Transport Mechanisms, Pharmaceutical Technology, Sep. 1999, pp. 120-.

* cited by examiner

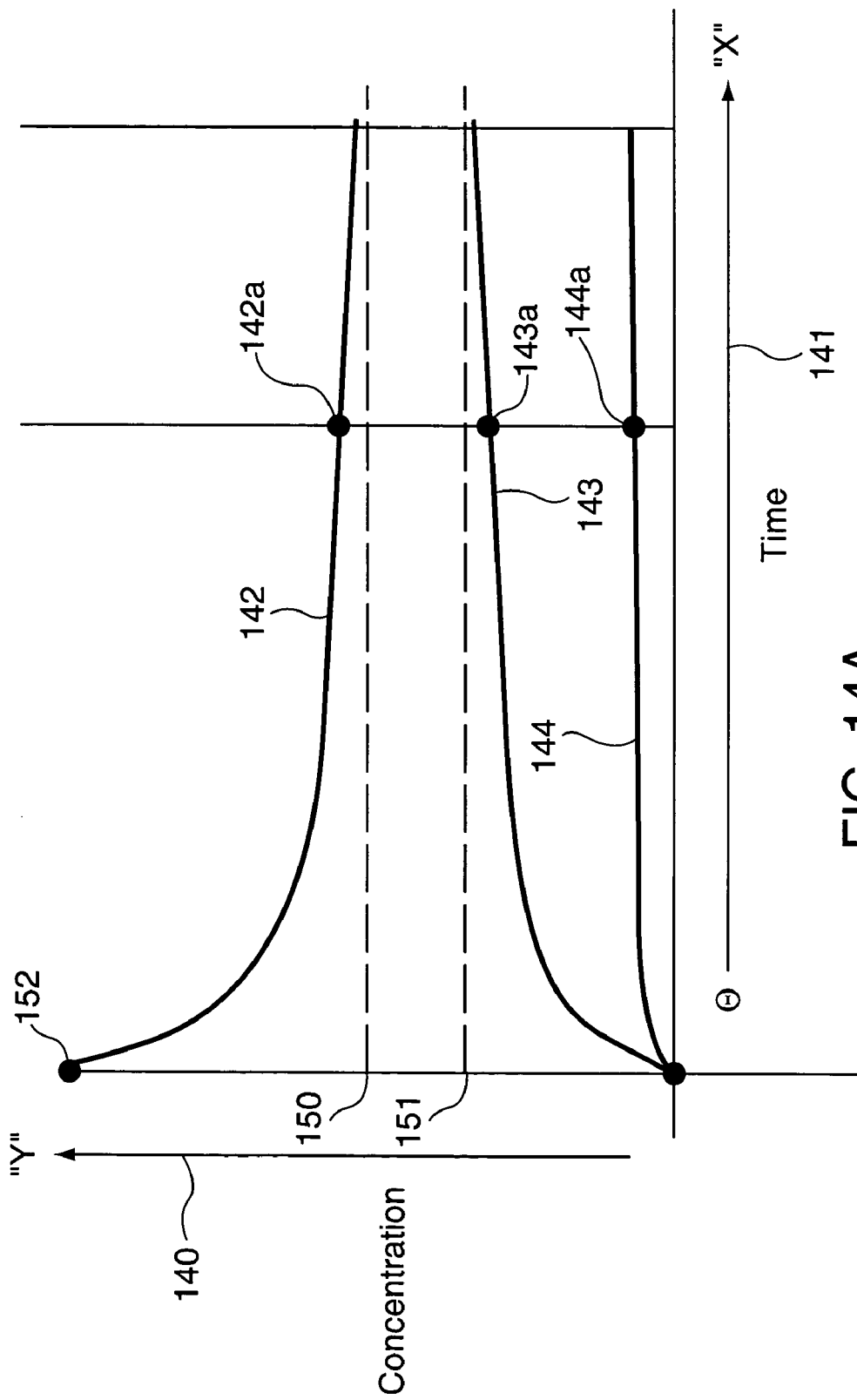

PARTICULATE FRAGRANCE DEPOSITION ON SURFACES AND MALODOUR ELIMINATION FROM SURFACES

FIELD OF THE INVENTION

Our invention is directed to a process for imparting an aesthetically-pleasing fragrance to, and/or substantially eliminating or covering a perceived malodour from one or more solid surfaces [for example, aqueous surfactant-containing composition-treated surfaces including fabrics, solid surfaces, mammalian epidermis surfaces, washing and/or conditioning and/or softening of fabrics, by means of carrying out the treatment using either (i) polymeric particles having internal free volumes which particles optionally contain within their respective free volumes controllably-releasable fragrance-imparting and/or malodour supressing or eliminating or covering compositions in a concentration of from about 0.5 weight % to about 50 weight % based on particle weight or (ii) an aqueous suspension prepared by causing to be suspended in the aqueous surfactant-containing treatment composition polymeric particles which (a) contain within the free volume thereof controllably-releasable fragrance-imparting and/or malodour-supressing or eliminating or covering compositions in a concentration of from about 0.5 weight % to about 50 weight % based on particle weight and/or (b) entrap within the free volume thereof fragrance imparting compositions absorbed from the surfactant-containing treatment composition for delivery to the surface to be treated and/or (c) entrap within the free volume thereof malodour components from the surfaces which are treated.] The fragrance imparting and/or malodour-supressing or eliminating or covering compositions initially or subsequently contained within the free volumes of the polymer particles or malodour molecules initially present on said surfaces are compatible with the polymer(s) which make up the infrastructures of the particles. The polymers which are useful in the practice of our invention are polyvinyl acetate-ethylene copolymers, ethylcellulose, polystyrene and polymethyl methacrylate. Our invention is also directed to the novel compositions which comprise the aforementioned polymeric particles in admixture with aqueous surfactant-containing compositions, including detergents, hair care compositions, fabric softener compositions and the like.

BACKGROUND OF THE INVENTION

The need for imparting substantive fragrances to, and removing or covering a perceived malodour from solid or semi-solid surfaces including fabric surfaces such as surfaces of articles of clothing being washed, the human epidermis, hair follicles and solid surfaces such as tile kitchen counters has been, over the past century, well-recognized in the prior art. Various attempts at fulfilling these needs using various delivery systems have been disclosed in the prior art.

There is a substantial presence in the international market place of fabric conditioning sheets containing perfumes intended for delivery to surfaces, for example, (a) products marketed under the trademark SNUGGLES (Lever Brothers, New York, N.Y.) described in U.S. Pat. Nos. 6,133,226 and 6,297,210 and (b) the products disclosed in published applications for U.S. Patent Applications 2003/0013632 and 2003/0069164. Furthermore, there is a substantial presence in the international market place of fabric conditioning liquids containing perfumes for delivery to solid and/or semisolid surfaces such as fabric surfaces, for example, products marketed under the trademark, DOWNY (Procter & Gamble, Cincinnati, Ohio) and described in U.S. Pat. Nos. 4,424,134 and 5,574,179.

The aforementioned published U.S. Patent Application 2003/13632 discloses a fabric conditioning article for use in a clothes dryer having a flexible sheet and a fabric conditioning composition deposited thereon including a fabric conditioning agent and perfume particles which are perfume compositions incorporated into porous mineral carriers. Other fragrance delivery systems for delivering fragrance compositions to a surface such as a fabric surface are disclosed in published European Patent Application 1 061 124 A1 and published U.S. Patent Application 2002/0016269. In paragraphs 0033 and 0035 of published U.S. Patent Application 2002/0016269 it is stated:

"[0033] One key embodiment . . . relates to the sustained release of fragrance on fabric wherein . . . particles are delivered via fully formulated detergent compositions . . . "

[0035] The particles which comprise the fragrance delivery systems . . . comprise an polymer or copolymer which can suitably absorb and deliver the fragrance benefits described herein to fabric. The . . . resulting polymer has the ability to carry one or more fragrance raw materials to a fabric and release said materials once delivered . . . "

The use of currently-marketed fabric conditioner sheets as exemplified herein as well as the uses as set forth in the prior art of fragrance-containing particles, for example, particles, the infrastructures of which are porous mineral materials or cyclodextrins, has, however, been determined to be inadequate for imparting aesthetically pleasing substantive fragrances to, and/or substantially eliminating or covering perceived malodours from solid or semi-solid surfaces such as aqueous surfactant-containing composition-treated fabrics.

Nothing in the prior art discloses or suggests a method for imparting substantive fragrances to, and/or removing or covering perceived malodours from solid or semi-solid surfaces using polymeric particles each of which has a free volume, where the polymers which compose the infrastructures of the particles are compatible with (a) malodour substances absorbable into the particle free volumes, and/or (b) fragrances releasably contained in the free volumes of the particles and/or (c) fragrances absorbable into the free volumes of the particles and subsequently releasable therefrom.

SUMMARY OF THE INVENTION

Our invention is directed to a process for imparting an aesthetically-pleasing substantive fragrance to, and/or substantially removing or covering a perceived malodour from one or more solid or semi-solid surfaces comprising the steps of:
  i. providing a plurality of solid and/or viscoelastic polymer (a) having a volume average diameter of from about 0.01 microns to about 1000 microns; (b) having a solid infrastructure which is composed of a substance selected from the group consisting of an ethylene-vinyl acetate copolymer containing from about 10% to about 90% vinyl acetate monomeric units, an ethyl cellulose polymer, a polystyrene polymer and a polymethyl methacrylate polymer, each of said polymers having a number average molecular weight of from about 8000 to about $1 \times 10^6$ and (c) having a substantially solid or viscoelastic three-dimensional porous infrastructure surrounding a free volume;

ii. optionally including in the solid or viscoelastic infrastructure free volume a fragrance composition, each of the components of which is compatible with said polymer;

iii. effecting deposition of said plurality of polymer particles onto said surface wherein fragrance components and malodour molecules are compatible with said polymer.

Optionally, each of the infrastructures of each of the polymer particles comprises a filler which creates a diffusion barrier and which increases the impact resistance and the modulus of elasticity of each of the polymer particles. Examples of such fillers are $SiO_2$, $CaCO_3$, $MgCO_3$, $Al_2O_3$, MgO, ZnO, $TiO_2$, surface-modified silicas, zeolites (hydrated alkali metal-aluminum silicates), clays, modified clays, wood flour, gypsum ($CaSO_4.2H_2O$) and activated carbon.

Each of the infrastructures of each of the polymer particles may contain, in addition, a solvent, for example, one or more of isopropyl myristate, diethyl phthalate, dibutyl phthalate, diisopropyl adipate, benzyl benzoate, mineral oil, a methyl ester of a vegetable-derived $C_{12}$–$C_{18}$ carboxylic acid, for example, "soybean methyl ester", the methyl ester of a mixture of 26% oleic acid, 49% linleic acid, 11% linolenic acid and 14% saturated fatty acids and a glyceryl ester of a vegetable-derived $C_{10}$ carboxylic acid, preferably the triglyceride of a 50:50 mixture of caprylic acid and capric acid marketed under the trademark, NEOBEE-M5 (Stepan Chemical Company, Northfield, Ill.).

The free volume of a polymer is estimated by comparing the density of a crystalline polymer versus that of the same polymer in the amorphous state, according to:

Free Volume (ml/100 g polymer)=$100 \times [1/\rho_a - 1/\rho_c]$ where $\rho_a$ and $\rho_c$ are the densities of the amorphous and crystalline form of the polymer, respectively, since free volume is the space that cannot be efficiently filled up by a polymer due to its inability to pack into a 100% crystalline structure.

For purposes of practicing our invention, "compatibility" which is a measure of solubility/miscibility and non-reactivity of the fragrance and the polymer is ascertained herein using the following approaches:

(1) Hildebrand or Hansen solubility parameters (group additivity method) as set forth in Barton, "CRC Handbook of Polymer-Liquid interaction Parameters and Solubility Parameters", 1990 by CRC Press, Inc. ISBN 0-8493-3544-2 pp. 11–15;

(2) UNIFAC (Unified quasi chemical theory of liquid mixtures Functional-group Activity Coefficients "UFAC") methods which utilize a group additivity principle by using the groups to add a non-ideal part to Flory's theory of polymer solubility as set forth in Gmehling et al., "Vapor-Liquid Equilibria by UNIFAC Group Contribution. Revision and Extension. 2" *Ind. Eng. Chem. Process. Des. Dev.* 1982, 21, 118–27. Furthermore, this method is based on a statistical mechanical treatment derived from the quasi chemical lattice model. In addition, this method includes a combinatorial and a "free volume" contribution (UNIFAC-FV); and (3) Monte Carlo/molecular dynamics techniques as set forth in Jacobson, Solomon H. "Molecular Modeling Studies of Polymeric Transdermal Adhesives: Structure and Transport Mechanisms" *Pharmaceutical Technology*, September 1999, pp 120, 122, 124, 126, 128 and 130.

More specifically, our invention provides alternative process embodiments:

(a) Applying particles each of which has a vacant free volume to solid or semi-solid surfaces which have adsorbed thereon malodourous substances. The malodourous substances, being compatible with the polymer particle infrastructures are absorbed into the particle free volumes;

(b) Placing particles, each of which has a vacant free volume into an aqueous emulsion containing fragrance substances and surfactant. The fragrance substances, being compatible with the polymer particle infrastructures are absorbed, for example, during storage or treatment, into the particle free volumes, and subsequently deposited onto solid or semi-solid surfaces such as fabrics being washed in a washing machine. After the fragrance deposition, malodour, if present, being compatible with the polymer, is absorbed into the free volume of the polymer;

(c) Placing particles, each of which has a free volume which contains a compatible fragrance composition, onto a solid or semi-solid surface. The fragrance composition is released from the polymer infrastructure and absorbed into the solid or semisolid surface and/or evolved into the environment immediately adjacent the solid or semi-solid surface, for example, the human epidermis or human hair via a hair care product. After the fragrance deposition, malodour, if present, being compatible with the polymer, is absorbed into the free volume of the polymer.

Thus, with respect to the above-mentioned embodiment, (b), our invention provides a process for imparting an aesthetically-pleasing substantive fragrance to, and/or substantially removing a perceived malodour from one or more aqueous surfactant-containing composition-treated solid or semi-solid surfaces during treatment of said surfaces with one or more surfactant-containing compositions comprising the steps of:

i. providing a plurality of polymer particles (a) having a volume average diameter of from about 0.01 microns to about 1000 microns; (b) having a solid or viscoelastic infrastructure which is composed of a substance selected from the group consisting of an ethylene-vinyl acetate copolymer containing from about 10% to about 90% vinyl acetate monomeric units, an ethylcellulose polymer, a polystyrene polymer and a polymethyl methacrylate polymer, each of said polymers having a number average molecular weight of from about 8000 to about $1\times10^6$ and (c) having a substantially solid or viscoelastic three-dimensional porous infrastructure surrounding a free volume;

ii. providing a surface treatment quantity of an aqueous composition comprising from about 1% up to about 25% by weight of at least one surfactant which aqueous composition is designed to be in intimate contact with said surfaces over a treatment period of time in a surface treatment concentration and temperature;

iii. providing treatment means for enabling treatment of said surfaces;

iv. introducing (a) said aqueous composition; (b) said surfaces; and (c) said plurality of particles into said treatment means;

v. engaging said treatment means for a treatment period of time at a treatment temperature;

vi. disengaging said treatment means;
vii. removing said surfaces from said treatment means;
viii. rinsing said surface; and
ix. drying said surface wherein fragrance components of fragrance compositions and malodour molecules are compatible with said polymers.

In this case, the treatment means is, for example, a washing machine, with the surface to be treated being a fabric being washed. At the end of the washing cycles, that is immediately subsequent to the rinse cycle, the polymer particles complete the release of fragrance onto the surface of the washed fabric; and, if malodour existed on the fabric, compatible malodour molecules are absorbed into the vacant free volumes of the polymer particles. In the alternative, if the surface is a hair follicle, the treatment means is a hair washing/rinsing procedure. Immediately subsequent to the rinse cycle, the polymer particles complete the release of fragrance onto the surface of each of the washed hair follicles; and, if malodour existed on the hair follicles, compatible malodour molecules are absorbed into the vacant free volumes of the polymer particles. Further in the alternative, if the surface is the human epidermis, and the treatment means is a bathing procedure, the polymer particles complete the release of fragrance onto the skin surface immediately subsequent to rinsing.

The following Table I sets forth publications which disclose fabric care, hair care and skin care procedures useful in the practice of our invention:

TABLE I

| Procedure Type | U.S. Pat. No. |
| --- | --- |
| fabric care | 4,318,818 |
| fabric care | 5,916,862 |
| skin care | 6,514,487 |
| hair care | 6,544,535 |
| hair care | 6,540,989 |
| skin care | 6,514,489 |
| skin care | 6,514,504 |
| skin care and hair care | 6,514,918 |
| hard surfaces | 6,514,923 |
| fabric care | 6,524,494 |
| hair care | 6,528,046 |
| skin and hair care | 6,531,113 |
| skin care | 6,551,604 |
| carpet care | 6,531,437 |

A preferred process of our invention for imparting an aesthetically-pleasing substantive fragrance to and/or substantially removing a perceived malodour from aqueous surfactant-containing composition-treated fabrics, hair follicles, mammalian epidermis or solid surfaces during treatment of said fabrics or hair follicles or mammalian epidermis or said solid surfaces with surfactant-containing compositions comprises the steps of:

i. providing a first plurality of polymer particles (a) having a volume average diameter of from about 0.01 microns to about 1000 microns, (b) having a solid or viscoelastic infrastructure which is composed of a an ethylene-vinyl acetate copolymer containing from about 10% to about 90% vinyl acetate monomeric units and having a number average molecular weight of from about 8000 to about $1 \times 10^6$ and (c) having a substantially solid or viscoelastic three-dimensional porous infrastructure having a free volume containing a liquid phase fragrance material removably entrapped in said infrastructure, contained in the interstices of said infrastructure and outwardly transportable from said infrastructure, each of the components of which fragrance material having a C $\log_{10}$ P in the range of from about 1 to about 7, the initial weight % of fragrance material contained in said plurality of polymer particles being from about 0.5% to about 50% by weight of the plurality of polymer particles, each of said fragrance components being compatible with said polymer;

ii. providing a second plurality of polymer particles (a) having a volume average diameter of from about 0.01 microns to about 1000 microns, (b) having a solid or viscoelastic infrastructure which is composed of an ethyl cellulose polymer having a number average molecular weight of from about 8000 to about $1 \times 10^6$ and (c) having a substantially solid or viscoelastic three-dimensional porous infrastructure surrounding a liquid phase fragrance material removably entrapped in said infrastructure, contained in the interstices of said infrastructure and outwardly transportable from said infrastructure, each of the components of which fragrance material having a C $\log_{10}$ P in the range of from about 1 to about 7, the initial weight % of fragrance material contained in said plurality of polymer particles being from about 0.5% to about 50% by weight of the plurality of polymer particles;

iii. mixing said first plurality of polymer particles with said second plurality of polymer particles to form a third plurality of polymer particles;

iv. providing a fabric, hair follicle, mammalian epidermis or solid surface treatment quantity of an aqueous composition comprising from about 1% to about 25% by weight of at least one surfactant which aqueous composition is designed to be in intimate treatment contact with either (a) at least one fabric article over a fabric treatment period of time in a fabric treatment concentration and temperature or (b) at least one solid surface over a solid surface treatment period of time in a solid surface treatment concentration and temperature or (c) at least one hair follicle over a hair follicle treatment period of time in a hair follicle treatment concentration and temperature or (d) a mammalian epidermis surface over a mammalian epidermis surface treatment period of time in a mammalian epidermis surface treatment concentration and temperature;

v. providing treatment means for enabling treatment of said fabrics, mammalian epidermis, hair follicles or said solid surfaces;

vi. introducing (a) said aqueous composition; (b) said at least one fabric article, hair follicle, mammalian epidermis or solid surface; and (c) said third plurality of polymer particles into said treatment means;

vii. engaging said treatment means for a treatment period of time at a treatment temperature;

viii. disengaging said treatment means;

ix. removing (a) said at least one fabric article or (b) said at least one solid surface or (c) said at least one hair follicle or (d) said mammalian epidermis from said treatment means;

x. rinsing (a) said at least one fabric article or (b) said at least one solid surface or (c) said at least one hair follicle or (d) said mammalian epidermis; and xi. drying (a) said at least one fabric article or (b) said at least one solid surface or (c) said at least one hair follicle or (d) said mammalian epidermis.

The infrastructures of the polymer particles useful in the practice of our invention may be composed of an ethylene-vinyl acetate copolymer containing from about 10% to about 90% vinyl acetate monomeric units, an ethylcellulose polymer, a polystyrene polymer polymer or a polymethyl methacrylate polymer or the particles may be composed of blends of any of the foregoing polymers. Preferably, the ethylene-vinyl acetate copolymers contain from about 65–75% ethylene monomeric moieties and from about 25–35% vinyl acetate monomeric moieties. A preferred ethylene-vinyl acetate copolymer is ELVAX 260 (E. I. Du Pont de Nemours & Co. Wilmington, Del.) having a melt index of 25 and 28% vinyl acetate monomeric units. A preferred polystyrene resin useful in the practice of our invention is STYRON 666D (The Dow Chemical Company, Midland, Mich.) having a melt flow rate of 8.00 g/10 minutes A preferred polymethyl methacrylate resin useful in the practice of our invention is ELVACITE 2041 (E. I. Du Pont de Nemours & Co. of Wilmington, Del.) having a number average molecular weight of 410,000. A preferred ethylcellulose resin useful in the practice of our invention is ETHOCEL Std.45 (The Dow Chemical Company, Midland, Mich.) having a viscosity range of 45–55 centipoises.

The polymer particles useful in the practice of our invention may be prepared according to a number of processes, for example:

(a) The plurality of polymer particles is produced by a process comprising the sequential steps of (a) blending polymer pellets with fragrance material for a period of time of from about 0.05 hours to about 20 hours; (b) extruding the resulting product at a temperature of from about 130° C. to about 170° C. to form an extrudate; (c) cooling the resulting extrudate to a temperature in the range of from about 15° C. to about 40° C. and (d) cryogrinding the resulting extrudate to form cryoground particles; or (b) The plurality of polymer particles is produced by a process comprising the sequential steps of (a) blending polymer pellets with silicon dioxide and fragrance material for a period of time of from about 0.05 hours to about 20 hours; (b) extruding the resulting product at a temperature of from about 130° C. to about 170° C. to form an extrudate; (c) cooling the resulting extrudate to a temperature in the range of from about 15° C. to about 40° C. and (d) cryogrinding the resulting extrudate to form cryoground particles;

(c) The plurality of polymer particles is produced by a process comprising the sequential steps of (1) extruding polymer pellets with one or more foam forming agents to from a foamed extrudate; (2) cooling the resulting extrudate to form an extrudate tow; (3) particularizing the resulting tow to form microporous polymer particles; and (4) admixing the resulting particles with a fragrance composition, the components of which are compatible with the polymer;

(d) In the case of using polymer particles, the infrastructures of which are each composed of polymethyl methacrylate, the polymmethyl methacrylate polymer particles are produced according to a process comprising the sequential steps of:

(1) milling polymethyl methacrylate to provide polymethyl methacrylate particles having an average effective diameter in the range of from about 5 microns to about 100 millimeters; then (2) admixing the resulting particles with a plasticizing quantity, e.g., from about 50% by weight of the particles to about 600% by weight of the particles, of a plasticizing composition which is a lower alkanol such as ethanol, n-propanal or isoproanol or a lower alkanone such as acetone, methyl ethyl ketone or methyl isobutyl ketone, or greater than about 10% aqueous solutions thereof, for example, 25%, 50%, 75% or 95%, preferably 50% aqueous ethanol solutions for a period of time of from about 30 seconds to about 10 minutes at a temperature in the range of from about 20° C. to about 45° C.; then, optionally (3) separating the plasticizing composition from the thus-treated polymer particles in order to form plasticizing compound-treated particles, and then, optionally (4) admixing the resulting plasticizing compound-treated polymer particles with a fragrance material which is compatible with the polymethyl methacrylate whereby a fragrance composition in a concentration of from about 0.5% to about 50% by weight of the filled particles is absorbed into the free volume of the polymethyl methacrylate polymer particles.

The foregoing polymer particle production processes as well as other particle production processes useful for producing polymer particles useful in the practice of our invention are set forth in the references listed in the following Table II:

TABLE II

| Polymer Type or Polymer Particle Production Type | U.S. Pat. No. or Other Reference Citation |
| --- | --- |
| ethylene-vinyl acetate copolymers(puffed using blowing agent) | U.S. Pat. No. 4,521,541 |
| ethyl cellulose | U.S. Pat. No. 6,509,034 |
| polystyrene | U.S. Pat. No. 4,247,498 |
| polymethyl methacrylate | U.S. Pat. No. 4,247,498 |

Other particle production processes useful for producing polymer particles useful in the practice of our invention are set forth in U.S. Pat. Nos. 3,505,432; 4,731,243; 4,934,609 and 6,213,409.

Each of the efficaciously releasable components of the fragrance composition absorbed into the free volumes of the polymeric particles useful in the practice of our invention has a $C \log_{10} P$ (calculated logarithm of base 10 of the n-octanol/water partition coefficient) of between 1 and 7, according to the inequality: $1 \leq C \log_{10} P \leq 7$. The range of fragrance composition in the polymeric particle is from about 0.5% by weight of the particle to about 45% by weight of the particle. The values of $\log_{10} P$ with respect to fragrance components are discussed in detail in U.S. Pat. Nos. 5,540,853 and 6,451,065 and Published Application 2003/0005522. Specific examples of fragrance components useful in the practice of our invention and the value of the $C \log_{10} P$'s thereof are as follows:

TABLE III

| Fragrance Component | $C \log_{10} P$ value |
| --- | --- |
| p-t-butyl-α-methylhydrocinnamaldehyde (hereinafter referred to as LILIAL (Givaudan-Roure Corporation of Clifton, N.J.) | 3.858 |
| 3-methyl-4-(2,6,6-trimethyl-2-cyclohexen-1-yl)-3-buten-2-one (Gamma methyl ionone) | 4.309 |
| n-hexyl salicylate | 5.260 |
| benzaldehyde | 1.480 |
| cis-jasmone | 2.712 |
| benzophenone | 3.120 |
| nerol | 2.649 |
| myristicin | 3.200 |
| amyl salicylate | 4.601 |
| cedryl acetate | 5.436 |
| cyclopentadecanolide | 6.246 |

TABLE III-continued

| Fragrance Component | C $\log_{10}$P value |
|---|---|
| linalyl benzoate | 5.233 |
| β-caryophyllene | 6.333 |

Examples of other fragrance components useful in the practice of our invention are dihydromyrcenol, a mixture of hexahydro-4,7-methanoinden-5-yl acetate and hexahydro-4,7-methanoinden-6-yl acetate (CYCLACET (International Flavors & Fragrances Inc., New York, N.Y.)), 2,4-dimethyl-3-cyclohexene-1-carboxaldehyde (ALDEHYDE AA (International Flavors & Fragrances Inc., New York, N.Y.)), the methyl ester of 3-oxo-2-n-pentylcyclopentane acetic acid (HEDIONE (Firmenich, Incorporated, Plainsboro, N.J.)) and α-methyl-3,4-methylenedioxy-hydrocinnamaldehyde (HELIONAL (International Flavors & Fragrances, New York, N.Y.)).

As illustrated by the graphs in FIGS. 14A and 14B, the process of our invention may be operated according to the mathematical model system:

$$m_P \int_0^\theta \left(\frac{\partial C_P}{\partial \theta}\right)_{C_S, C_W} d\theta + m_W \int_0^\theta \left(\frac{\partial C_W}{\partial \theta}\right)_{C_P, C_S} d\theta + m_S \int_0^\theta \left(\frac{\partial C_S}{\partial \theta}\right)_{C_P, C_W} d\theta = C_T m_T$$

for the fragrance composition; and $$\sum_{i=1}^{n} (m_p + C_{pi} + m_{wi}C_{wi} + m_s C_{si}) = C_T m_T \text{ for "n"}$$

individual fragrance components wherein $1 \leq i \leq n$
wherein θ represents time in hours;
wherein $C_P$ represents the fragrance concentration in the polymer particle in grams/liter;
wherein $$\frac{\partial C_P}{\partial \theta}$$

represents the partial derivative of fragrance concentration in the polymer particle with respect to time, measures in grams/liter-hour;
wherein $C_w$ represents the fragrance concentration in the water phase in grams/liter;
wherein $$\frac{\partial C_w}{\partial \theta}$$

represents the partial derivative of fragrance concentration in the water phase with respect to time measured in grams/liter-hour;
wherein $C_S$ represents the fragrance concentration in the surfactant phase in grams/liter;

wherein $$\frac{\partial C_S}{\partial \theta}$$

represents the partial derivative of fragrance concentration in the surfactant phase with respect to time measured in grams/liter-hour;
wherein $C_T$ represents the total concentration of fragrance in the system in grams/liter;
wherein $m_P$ represents the mass of the polymer particles in grams.;
wherein $m_S$ represents the surfactant mass in grams;
wherein $m_W$ represents the water mass in grams; and
wherein $m_T$ represents the total system mass in grams with all terms being measured at a point in time, θ.

In the mathematical model, $$m_P \int_0^\theta \left(\frac{\partial C_P}{\partial \theta}\right)_{C_S, C_W} d\theta + m_W \int_0^\theta \left(\frac{\partial C_W}{\partial \theta}\right)_{C_P, C_S} d\theta + m_S \int_0^\theta \left(\frac{\partial C_S}{\partial \theta}\right)_{C_P, C_W} d\theta = C_T m_T$$

as shown in FIG. 14A:

$C_P = -k_1 LN(\theta+1) + k_2$ with $0.015 \geq k_1 \geq 0.03$ and $0.18 \geq k_2 \geq 0.22$;

$C_S = k_3 LN(\theta+1) + k_4$ with $1.5 \times 10^{-3} \geq k_3 \geq 2.2 \times 10^{-3}$ and $1.2 \times 10^{-4} \geq k_4 \geq 2.0 \times 10^{-4}$; and $C_W = k_5 LN(\theta+1) + k_6$ with $1.5 \times 10^{-6} \geq k_5 \geq 3.0 \times 10^{-6}$ and $1.5 \times 10^{-7} \geq k_6 \geq 3.0 \times 10^{-7}$

BRIEF DESCRIPTION OF THE DRAWINGS

FIG. 14A sets forth, for a polymer particle-water-detergent system, graphs of fragrance concentration vs. time (in hours) for polymer particles initially containing fragrance components in their free volumes, detergent particles initially not containing any fragrance and for water initially not containing any fragrance.

DETAILED DESCRIPTION OF THE INVENTION

Figure 1:
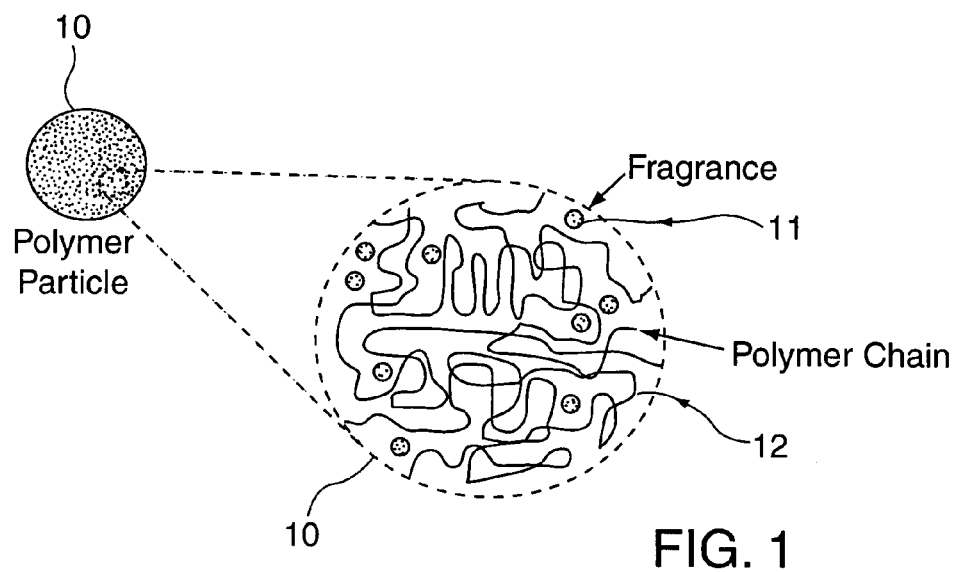
FIG. 1 is a schematic view of a polymer particle useful in the practice of our invention.

Referring to FIG. 1 the schematic view of a polymer particle 10 useful in the practice of our invention, the polymer chain is indicated by reference numeral 12 and the fragrance contained in the particle's free volume is indicated by reference numeral 11.

Figure 2:
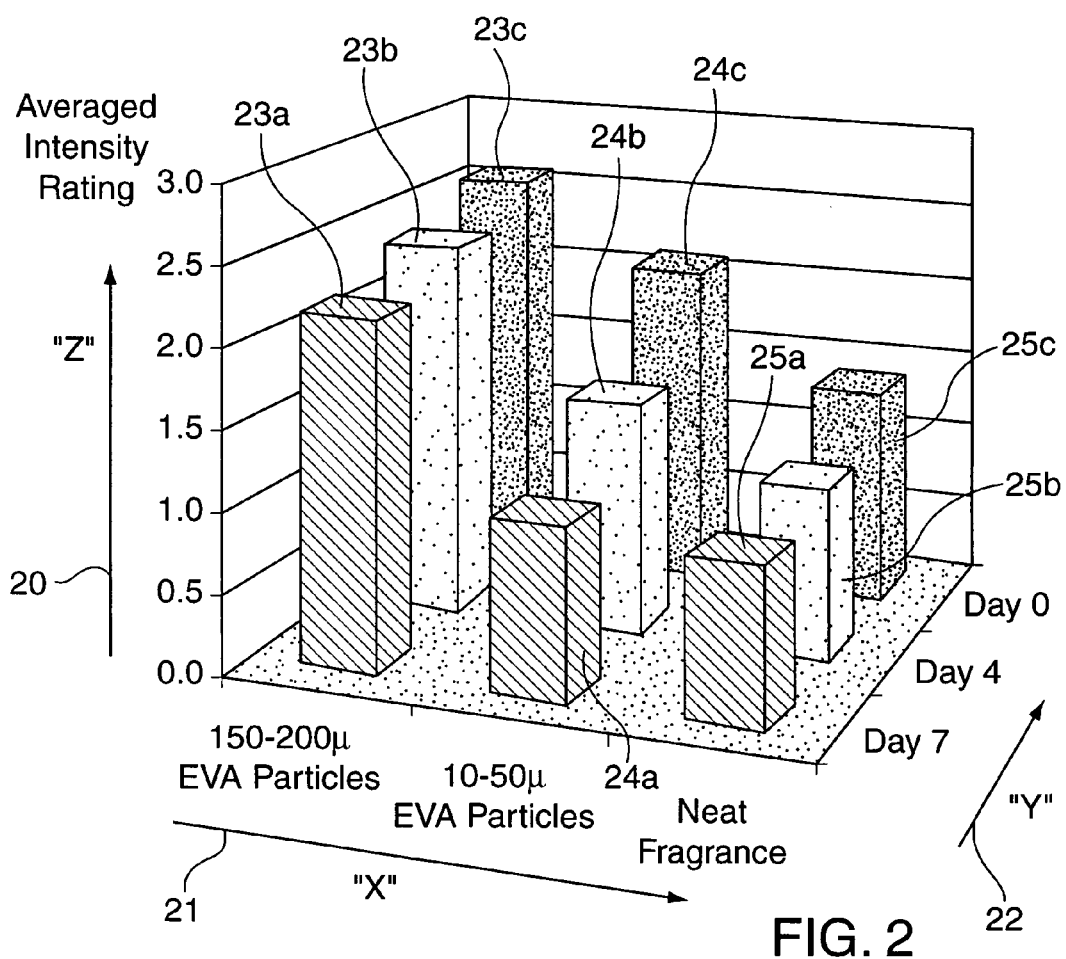
FIG. 2 is a group of bar graphs shown in 3 dimensions: nature of fragrance evolving material, e.g., polymer or neat fragrance on the "X" axis; number of days of use on the "Y" axis and averaged intensity rating on the "Z" axis.

Referring to FIG. 2, the group of bar graphs shown in 3 dimensions, the nature of fragrance evolving material, e.g., polymer or neat fragrance is shown on the "X" axis indicated by reference numeral 21; the number of days of use is shown on the "Y" axis indicated by reference numeral 22 and the averaged intensity rating is shown on the "Z" axis indicated by reference numeral 20. The bar graphs for the fragrance-containing ethylene-vinyl acetate copolymer 150–200 micron particles (hereinafter referred to as "EVA particles") are indicated by reference numerals 23a, 23b and 23c for, respectively, days 7, 4 and 0. The bar graphs for fragrance-containing EVA 10–50 micron particles are indicated by reference numerals 24a, 24b and 24c for, respectively, days 7, 4 and 0. The bar graphs for the neat fragrance are indicated by reference numerals 25a, 25b and 25c for, respectively, days 7, 4 and 0.

Figure 3:
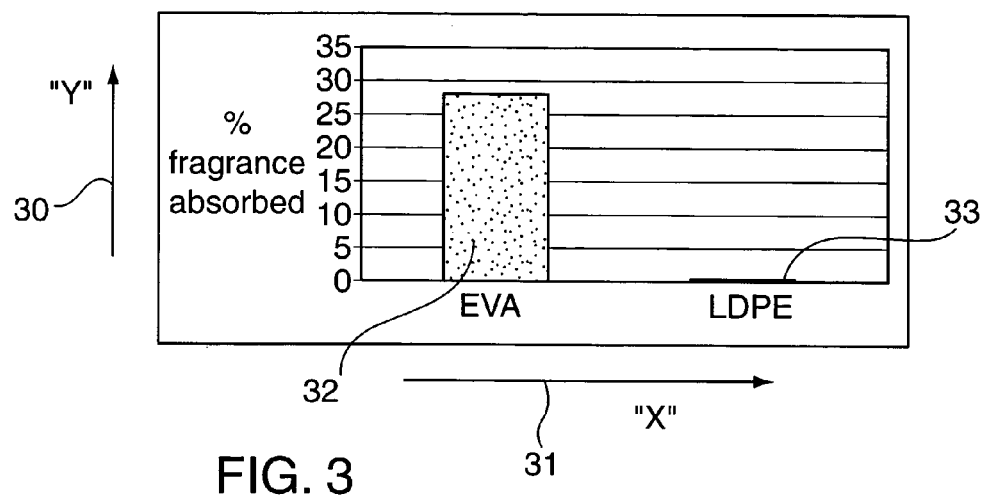
FIG. 3 is a bar graph chart showing a comparison of % fragrance absorbed for an ethylene-vinyl acetate copolymer vs. low density polyethylene.

Referring to FIG. 3, the bar graph chart showing a comparison of % fragrance absorbed (on the "Y" axis, indicated by reference numeral 30) for an ethylene-vinyl acetate copolymer (indicated by reference numeral 32) vs. low density polyethylene (indicated by reference numeral 33), with the nature of the polymer set forth along the "X" axis, indicated by reference numeral 31.

Figure 4:
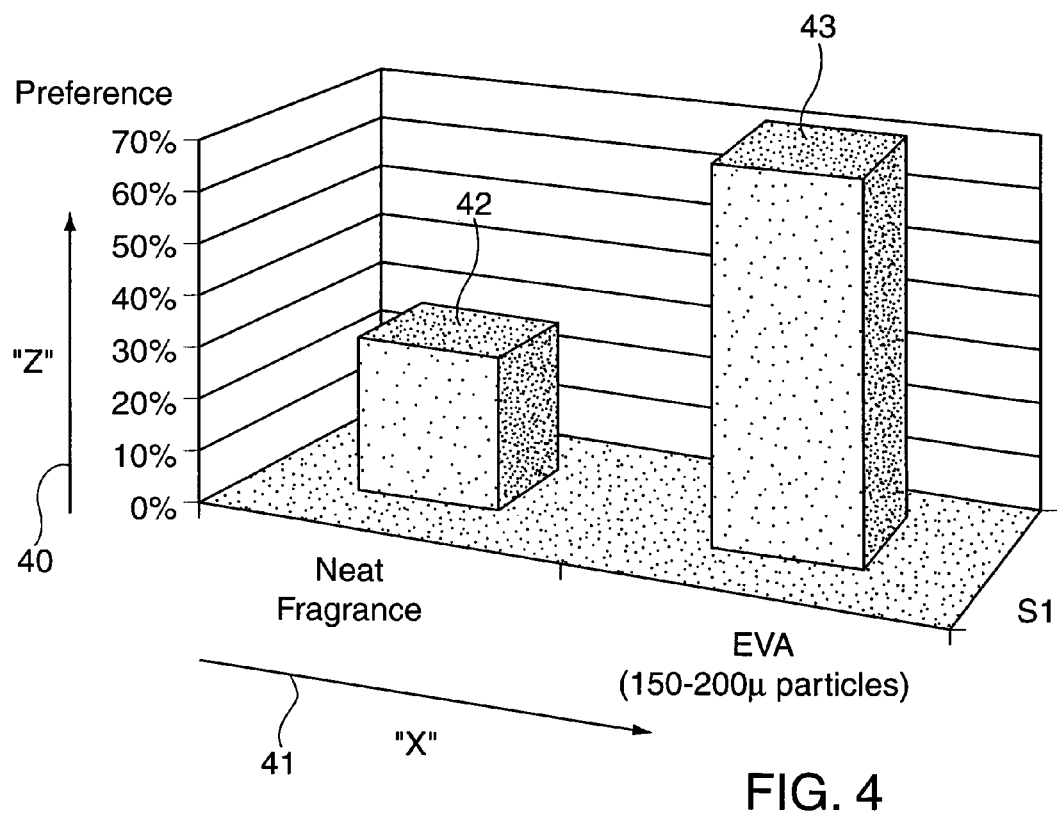
FIG. 4 is a bar graph chart showing a comparison of % preference for neat fragrance vs. ethylene-vinyl acetate copolymer particles containing the fragrance (150–200 microns mean effective diameter).

Referring to FIG. 4, the bar graph chart showing a comparison of % preference for neat fragrance (with % preference shown on the "Z" axis, indicated by reference numeral 40) vs. ethylene-vinyl acetate copolymer particles containing the fragrance (150–200 microns mean effective diameter), the bar graph for neat fragrance is shown by reference numeral 42 and the bar graph for the EVA particles is shown by reference numeral 43. The fragrance emitting substance is shown along the "X" axis, shown by reference numeral 41.

Figure 5:
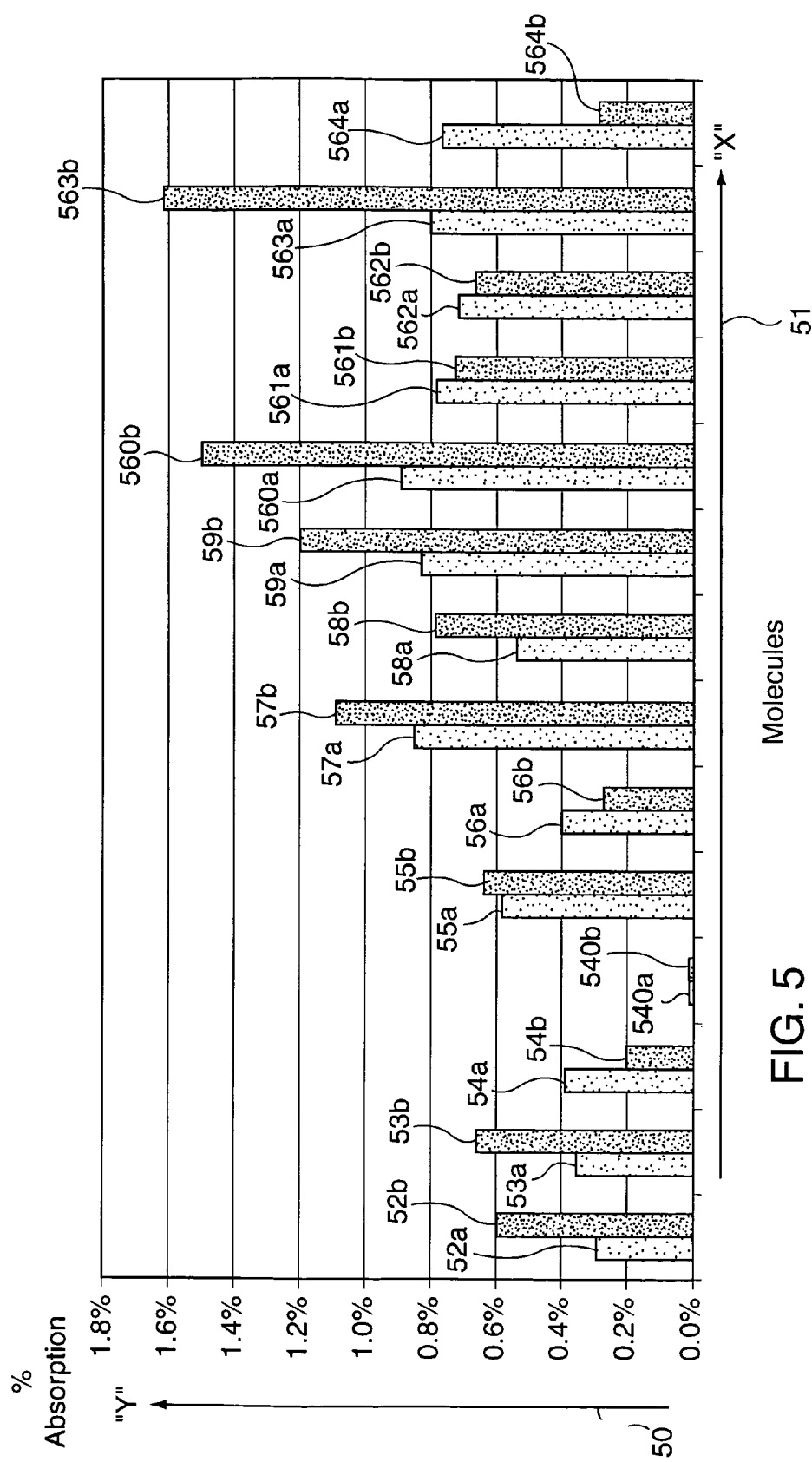
FIG. 5 is a bar graph chart showing % fragrance absorption in HTEAQ (hydrogenated triethanolamine ester quaternary ammonium salt base as described in U.S. Application 2003/0069164, e.g., VARISOFT WE-16 (Sherex Chemical, Inc., Dublin, Ohio) or STEPANTEX VQ-90 (Stepan Company, Northfield, Ill.) for ethylene-vinyl acetate copolymer vs. polystyrene for various fragrance components.

Referring to FIG. 5 a bar graph chart showing % fragrance absorption (shown on the "Y" axis, indicated by reference numeral 50) in HTEAQ base for ethylene-vinyl acetate copolymer vs. polystyrene for various fragrance components (shown along the "X" axis, indicated by reference numeral 51). The reference numerals for each fragrance component is given in the following Table IV:

TABLE IV

| Fragrance Component | EVA | Polystyrene |
|---|---|---|
| ethyl-2-methyl valerate | 52a | 52b |
| limonene | 53a | 53b |
| dihydromyrcenol | 54a | 54b |
| β-phenylethyl alcohol | 540a | 540b |
| benzyl acetate | 55a | 55b |
| geraniol | 56a | 56b |
| dimethyl benzyl carbinyl acetate | 57a | 57b |
| methyl nonyl acetaldehyde | 58a | 58b |
| CYCLACET | 59A | 59B |
| 2-methoxynaphthalene | 560a | 560b |
| β-ionone | 561a | 561b |
| LILIAL | 562a | 562b |
| n-hexyl salicylate | 563a | 563b |
| TONALID (6-acetyl-1,1,3,4,6,6-hexamethyl tetrahydronaphthalene (PFW Chemicals B.V., Barneveld, Netherlands)) | 564a | 564b |

Figure 6:
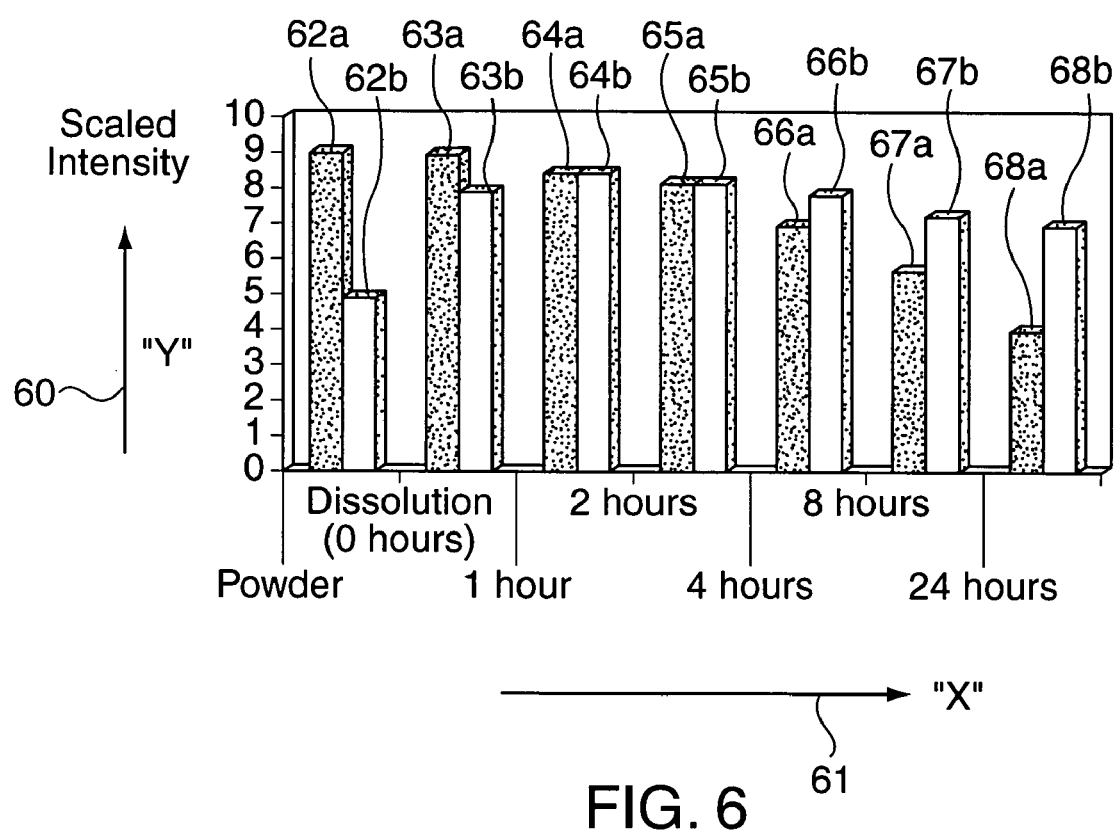
FIG. 6 is a bar graph chart showing scaled intensity (on a scale of 0–10, on the "Y" axis) vs. time (on the "X" axis), comparing fragrance release upon soak in an open tub for ethylene-vinyl acetate copolymer particles (containing a fragrance oil) (150–200 micron particles) vs. neat fragrance oil.

Referring to FIG. 6, a bar graph chart showing scaled intensity (on a scale of 0–10, on the "Y" axis, indicated by reference numeral 60) vs. time (on the "X" axis shown by reference numeral 61), comparing fragrance release upon soak in an open tub for ethylene-vinyl acetate copolymer particles (containing a fragrance oil) (150–200 micron particles) vs. neat fragrance oil each member of each group of bar graphs is indicated by a reference numeral as shown in Table V:

TABLE V

| Time | EVA | Neat Fragrance Oil |
|---|---|---|
| Powder (−1 hour) | 62b | 62a |
| Dissolution (0 hours) | 63b | 63a |
| 1 hour | 64b | 64a |
| 2 hours | 65b | 65a |
| 4 hours | 66b | 66a |
| 8 hours | 67b | 67a |
| 24 hours | 68b | 68a |

Figure 7:
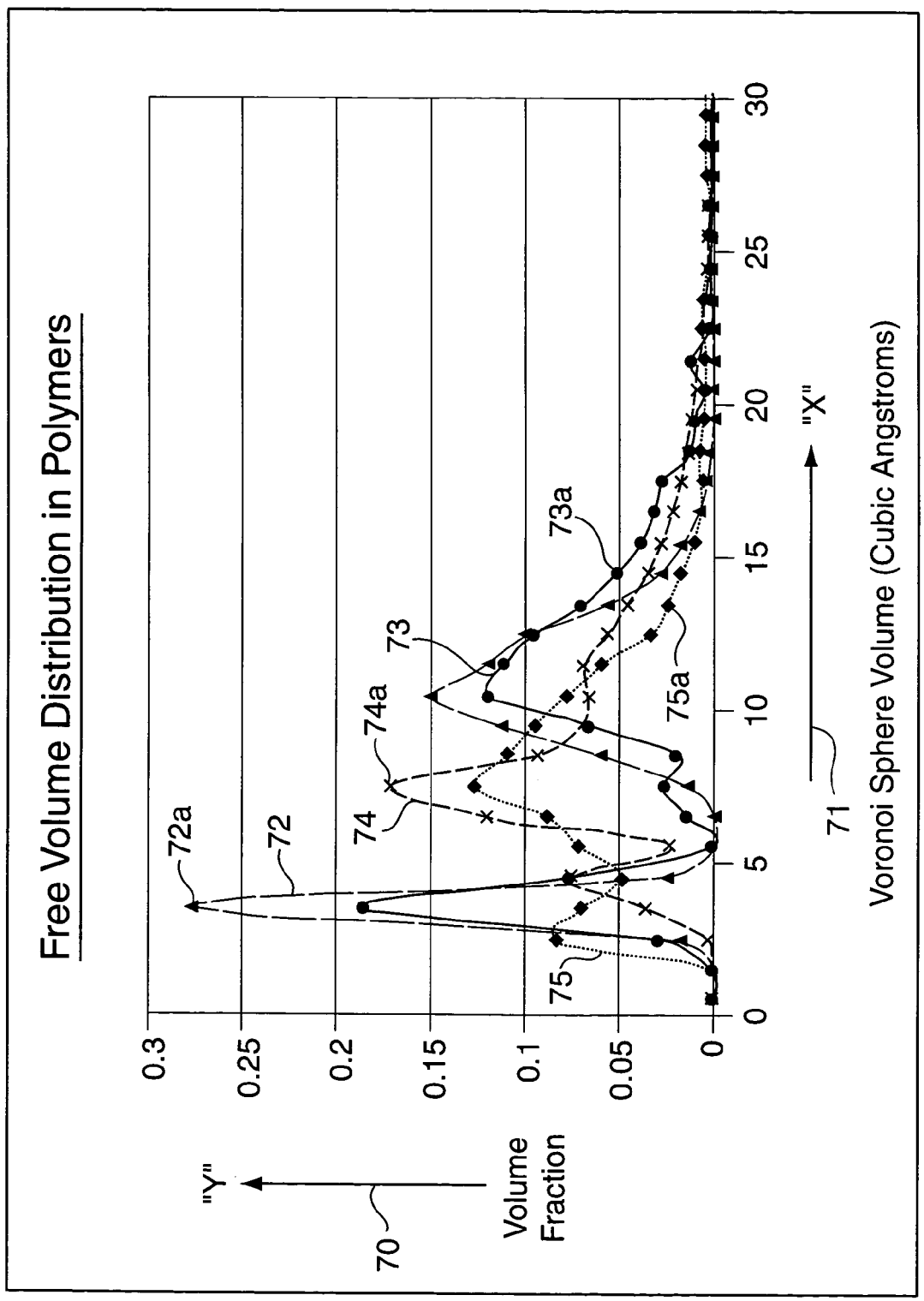
FIG. 7 is a set of graphs for free volume distribution in four polymers: polymethylmethacrylate; polyethylene; polystyrene and ethylene-vinyl acetate copolymer (28% vinyl acetate monomeric units) showing volume fraction (on the "Y" axis vs. Voronoi Sphere Volume (measured in cubic angstroms) on the "X" axis).

Referring FIG. 7, it is a set of four graphs for free column distribution in four polymers: polymethylmethacrylate (reference numeral 75 with illustrative data point 75a); polyethlene (reference numeral 72 with illustrative data point 72a); polystyrene (reference numeral 74 with illustrative data point 74a) and ethylene-vinyl acetate copolymer (28% vinyl acetate monomeric units) (reference numeral 73 with illustrative data point 73a) showing volume fraction (on the "Y" axis shown by reference numeral 70) vs. Voronoi Sphere Volume (measured in cubic angstroms) on the "X" axis (shown by reference numeral 71).

Figure 8:
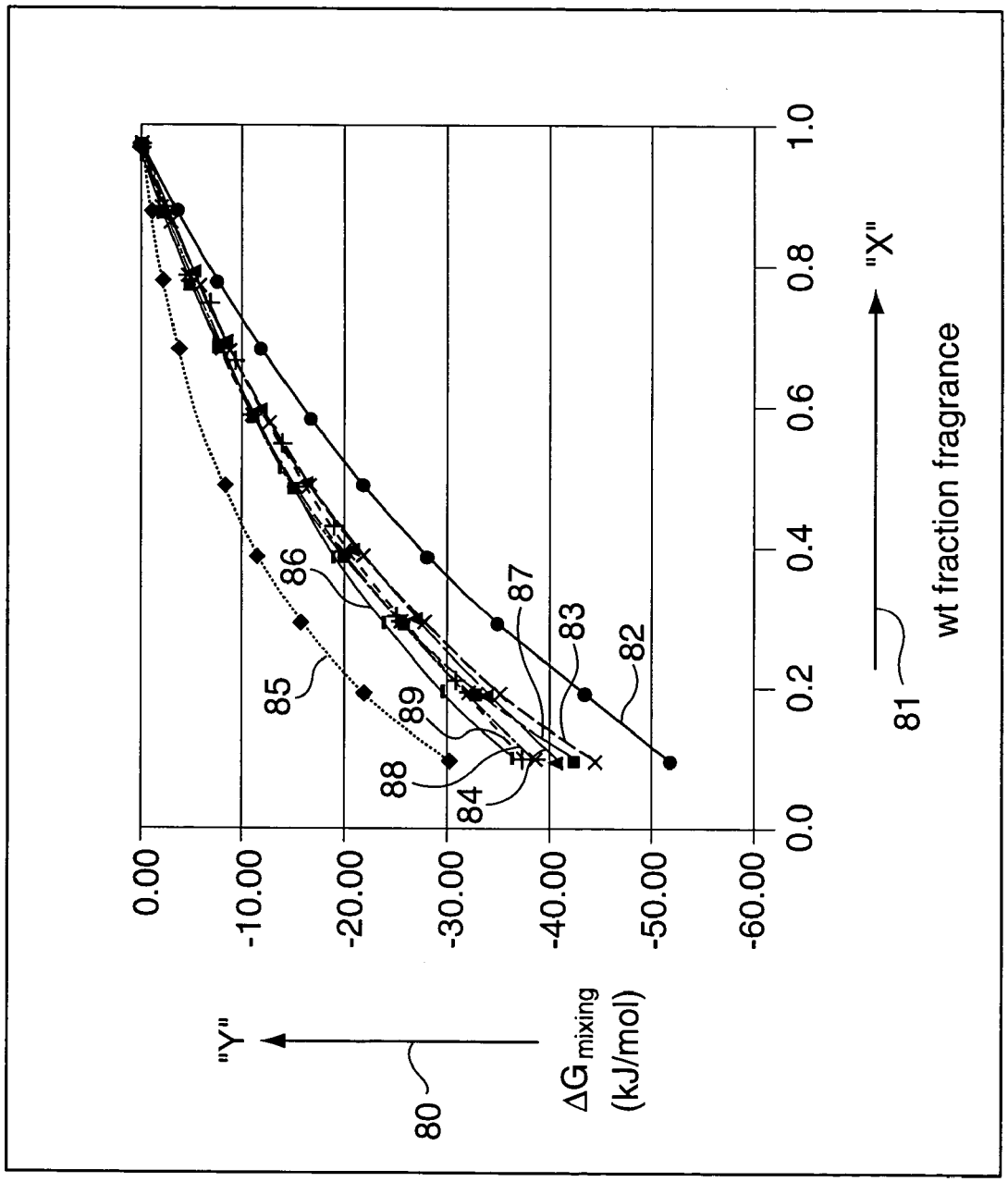
FIG. 8 is a set of 8 graphs, one for each fragrance component, showing calculated (using UNIFAC-FV) free energy of mixing of fragrances in an ethylene-vinyl acetate copolymer (28% vinyl acetate monomeric units), with free energy of mixing in kilojoules/mole on the "Y" axis and weight fraction of fragrance on the "X" axis.

Referring to FIG. 8, it is a set of 8 graphs, one for each fragrance component, showing calculated (using UNIFAC-FV) free energy of mixing of fragrances in an ethylene-vinyl acetate copolymer (28% vinyl acetate monomeric units), with free energy of mixing in kilojoules/mole on the "Y" axis (indicated by reference numeral 80) and weight fraction of fragrance on the "X" axis (indicated by reference numeral 81). The reference numerals defining each graph is shown in a table for FIGS. 8–12, inclusive, in Table VI.

Figure 9:
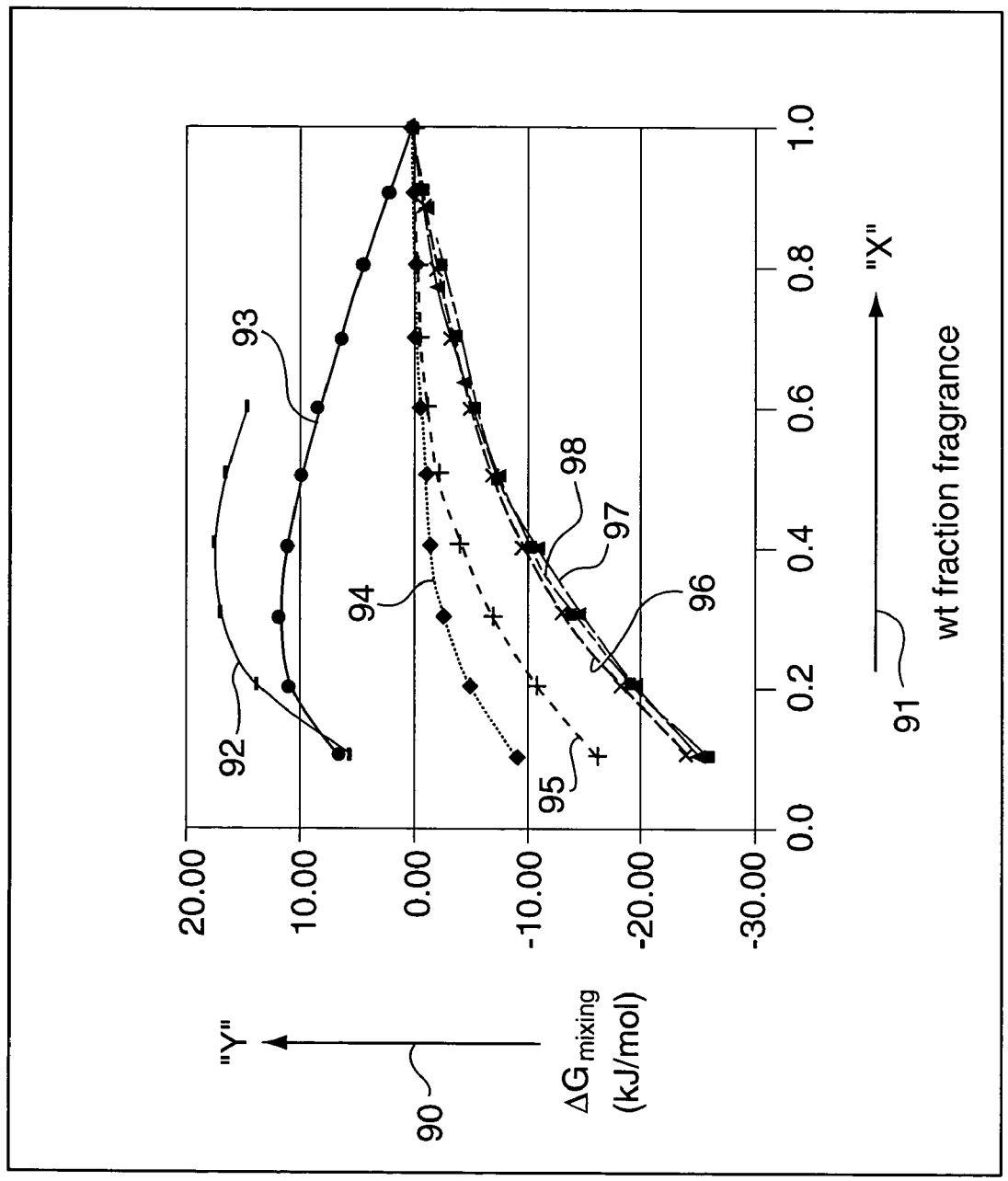
FIG. 9 is a set of 8 graphs, one for each fragrance component, showing calculated (using UNIFAC-FV) free energy of mixing of fragrances in a polyethylene polymer with free energy of mixing in kilojoules/mole on the "Y" axis and weight fraction of fragrance on the "X" axis.

FIG. 9 is a set of 8 graphs, one for each fragrance component, showing calculated (using UNIFAC-FV) free energy of mixing of fragrances in a polyethylene polymer with free energy of mixing in kilojoules/mole on the "Y" axis (indicated by reference numeral 90) and weight fraction of fragrance on the "X" axis (indicated by reference numeral 91). The reference numerals defining each graph is shown in a table for FIGS. 8–12, inclusive, in Table VI.

Figure 10:
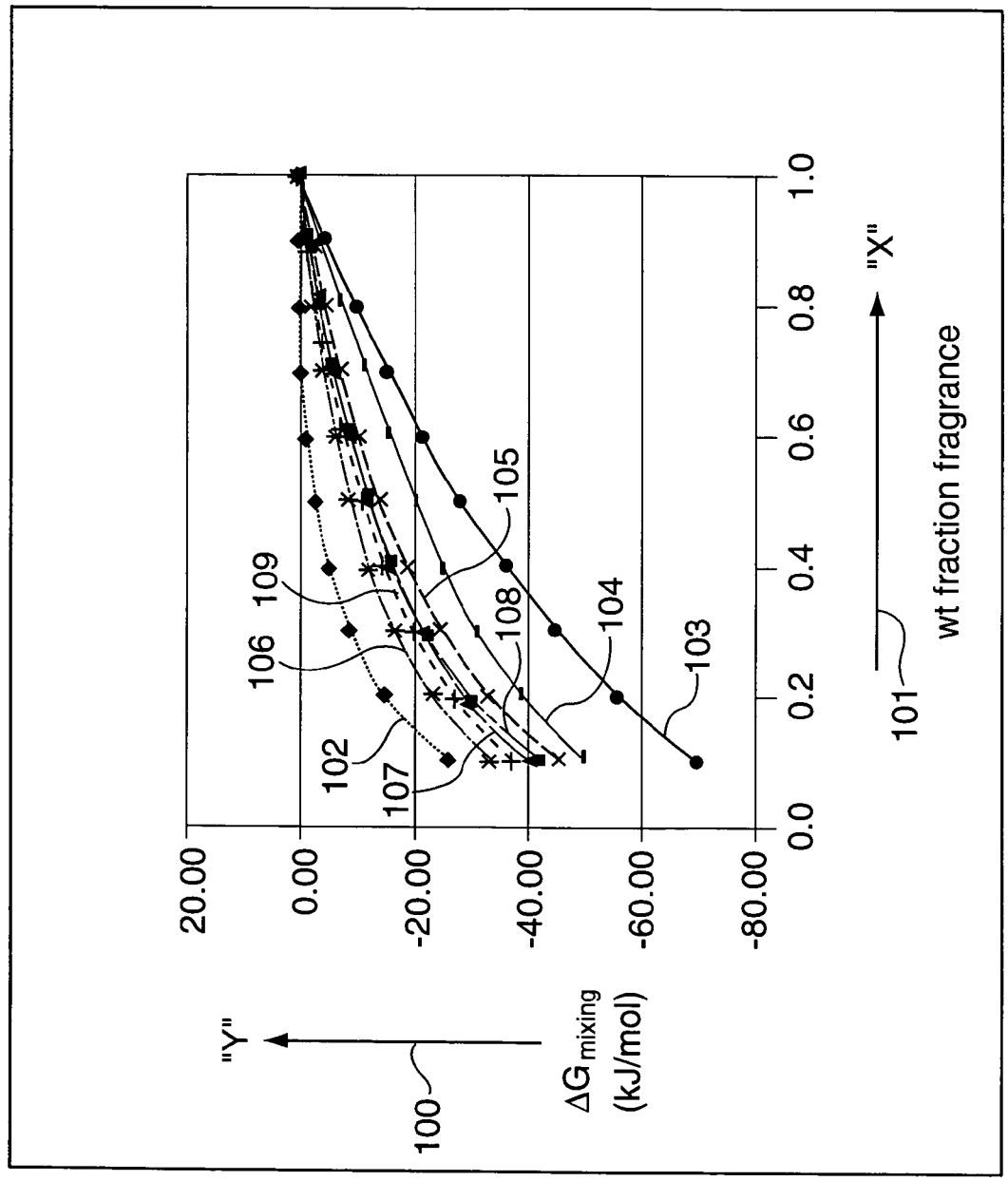
FIG. 10 is a set of 8 graphs, one for each fragrance component, showing calculated (using UNIFAC-FV) free energy of mixing of fragrances in a polymethyl methacrylate polymer with free energy of mixing in kilojoules/mole on the "Y" axis and weight fraction of fragrance on the "X" axis.

FIG. 10 is a set of 8 graphs, one for each fragrance component, showing calculated (using UNIFAC-FV) free energy of mixing of fragrances in a polymethyl methacrylate polymer with free energy of mixing in kilojoules/mole on the "Y" axis (indicated by reference numeral 100) and weight fraction of fragrance on the "X" axis (indicated by reference numeral 101). The reference numerals defining each graph is shown in a table for FIGS. 8–12, inclusive.

Figure 11:
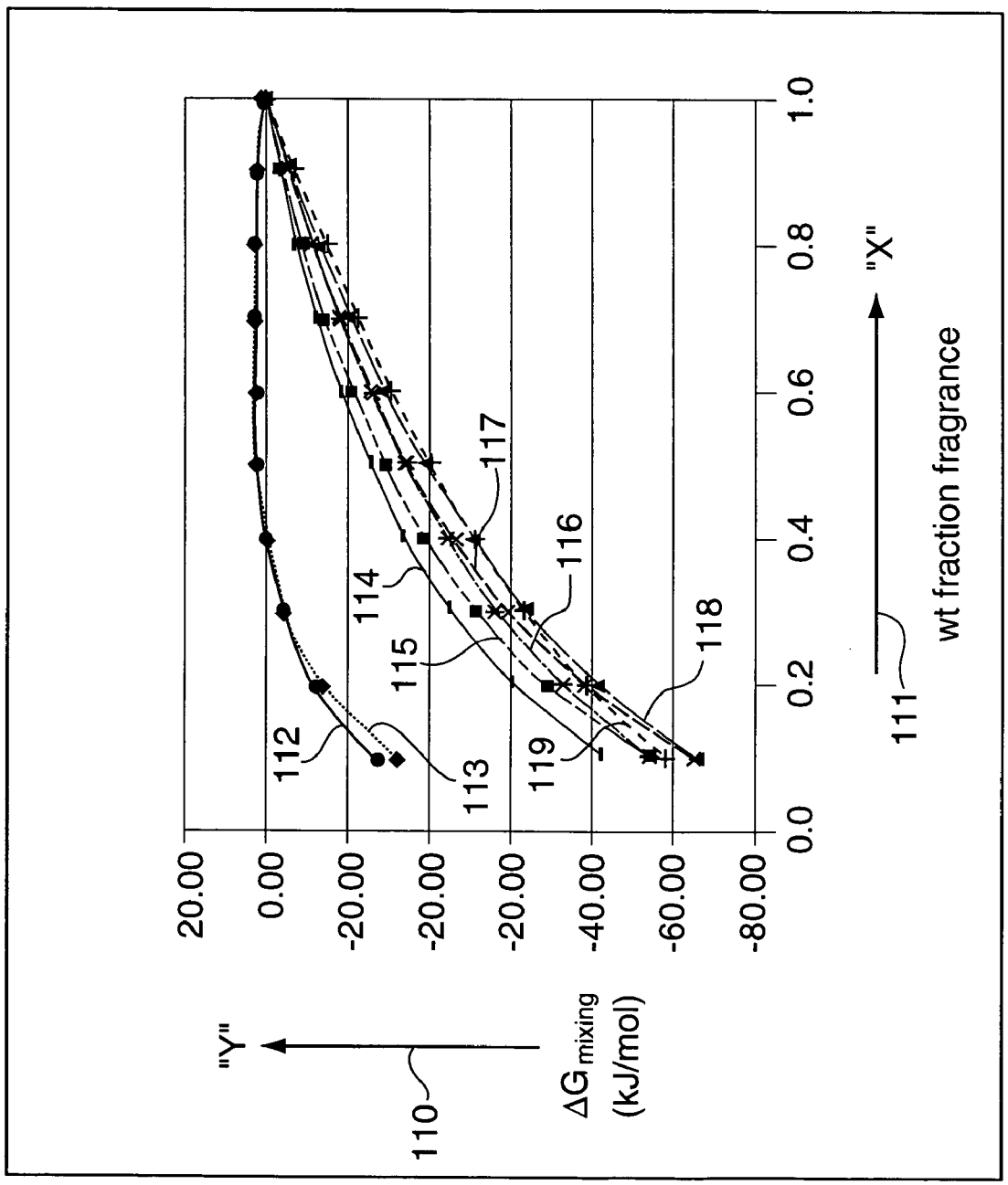
FIG. 11 is a set of 8 graphs, one for each fragrance component, showing calculated (using UNIFAC-FV) free energy of mixing of fragrances in a polystyrene polymer with free energy of mixing in kilojoules/mole on the "Y" axis and weight fraction of fragrance on the "X" axis.

FIG. 11 is a set of 8 graphs, one for each fragrance component, showing calculated (using UNIFAC-FV) free energy of mixing of fragrances in a polystyrene polymer with free energy of mixing in kilojoules/mole on the "Y" axis (indicated by reference numeral 110) and weight fraction of fragrance on the "X" axis (indicated by reference numeral 111). The reference numerals defining each graph is shown in a table for FIGS. 8–12, inclusive.

Figure 12:
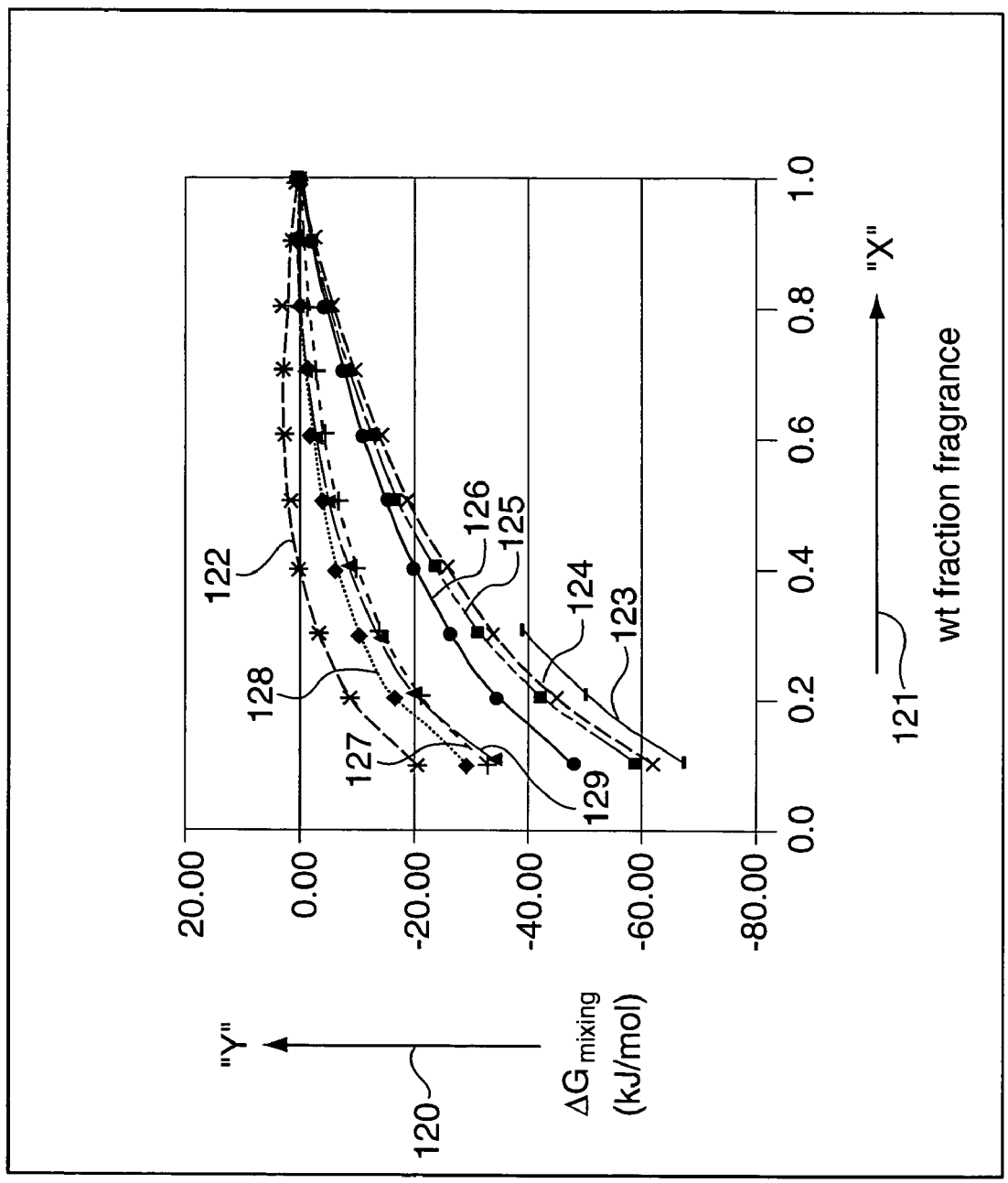
FIG. 12 is a set of 8 graphs, one for each fragrance component, showing calculated (using UNIFAC-FV) free energy of mixing of fragrances in an ethylcellulose polymer with free energy of mixing in kilojoules/mole on the "Y" axis and weight fraction of fragrance on the "X" axis.

FIG. 12 is a set of 8 graphs, one for each fragrance component, showing calculated (using UNIFAC-FV) free energy of mixing of fragrances in an ethylcellulose polymer with free energy of mixing in kilojoules/mole on the "Y" axis (indicated by reference numeral 120) and weight fraction of fragrance on the "X" axis (indicated by reference numeral 121). The reference numerals defining each graph is shown in a table for FIGS. 8–12, inclusive.

TABLE VI

| Fragrance Component | EVA (FIG. 8) | Polyethylene (FIG. 9) | Polymethyl-methacrylate (FIG. 10) | Polystyrene (FIG. 11) | Ethyl Cellulose (FIG. 12) |
|---|---|---|---|---|---|
| Dihydromyrcenol | 85 | 94 | 102 | 113 | 128 |
| LILIAL | 87 | 98 | 108 | 115 | 125 |
| CYCLACET | 84 | 97 | 107 | 118 | 129 |
| ALDEHYDE AA | 83 | 96 | 105 | 117 | 124 |
| γ-methyl ionone | 88 | — | 106 | 116 | 122 |
| n-hexyl salicylate | 82 | 93 | 103 | 112 | 126 |
| HEDIONE | 89 | 95 | 107 | 119 | 127 |
| HELIONAL | 86 | 92 | 104 | 114 | 123 |

Figure 13:
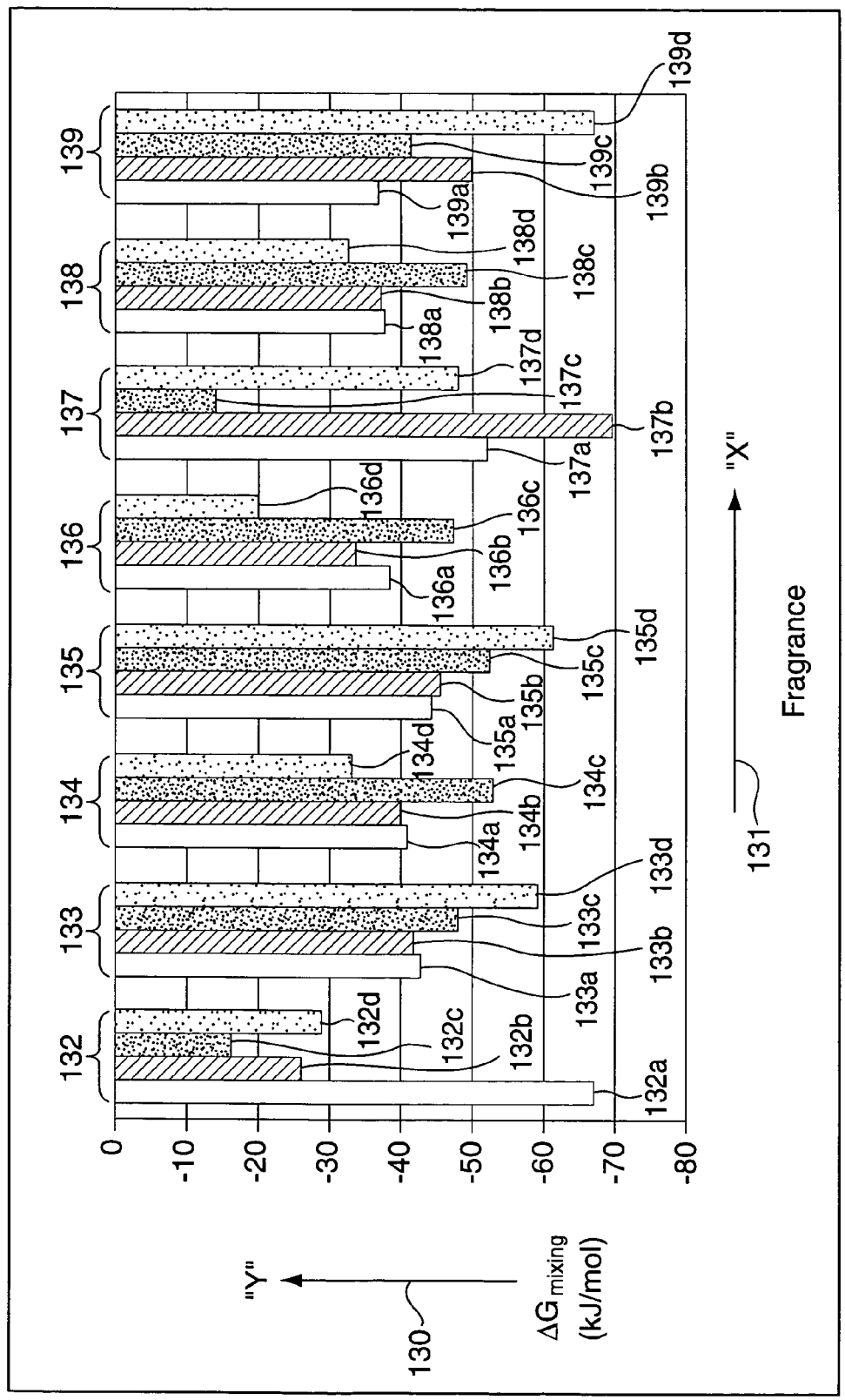
FIG. 13 is a set of bar graphs shown in eight groups, one for each fragrance, showing calculated (using UNIFAC-FV) free energy of mixing of fragrances in four different polymers with free energy of mixing in kilojoules/mole on the "Y" axis and setting forth fragrance component on the "X" axis.

Referring to FIG. 13, it is a set of bar graphs shown in eight groups, one for each fragrance, showing calculated (using UNIFAC-FV) free energy of mixing of fragrances in an four different polymers with free energy of mixing in kilojoules/mole on the "Y" axis (indicated by reference numeral 130) and setting forth fragrance component on the "X" axis (indicated by reference numeral 131). Reference numerals for each group of bar graphs and for each bar graph in each group for each fragrance component are set forth in the following Table VII:

TABLE VII

| Fragrance Component | Group of Bar Graphs | EVA | Polymethyl-methacrylate | polystyrene | ethyl cellulose |
|---|---|---|---|---|---|
| Dihydromyrcenol | 132 | 132a | 132b | 132c | 132d |
| LILIAL | 133 | 133a | 133b | 133c | 133d |
| CYCLACET | 134 | 134a | 134b | 134c | 134d |
| ALDEHYDE AA | 135 | 135a | 135b | 135c | 135d |

TABLE VII-continued

| Fragrance Component | Group of Bar Graphs | EVA | Polymethyl-methacrylate | polystyrene | ethyl cellulose |
|---|---|---|---|---|---|
| γ-methyl ionone | 136 | 136a | 136b | 136c | 136d |
| n-hexyl salicylate | 137 | 137a | 137b | 137c | 137d |
| HEDIONE | 138 | 138a | 138b | 138c | 138d |
| HELIONAL | 139 | 139a | 139b | 139c | 139d |

Referring to FIG. 14A, it sets forth, for a polymer particle-water-surfactant system, graphs of fragrance concentration (on the "Y" axis, indicated by reference numeral 140) vs. time (in hours) (on the "X" axis indicated by reference numeral 141) for polymer particles initially containing fragrance components in their free volumes (the graph being indicated by reference numeral 142 with a data point a 0 hours being indicated by reference numeral 152 and with a data point at about 150 hours being indicated by reference numeral 142a), surfactant phase (e.g., containing micelles and/or vesicles) initially not containing any fragrance (the graph being indicated by reference numeral 143 with a data point at about 150 hours being indicated by reference numeral 143a) and for water initially not containing any fragrance (the graph being indicated by reference numeral 144 with a data point at about 150 hours being indicated by reference numeral 144a). Line 150 represents a concentration of about 8%, as asymptote approached by the fragrance concentration in the polymer particle at θ=∞. Line 151 represents an asymptote approached by fragrance concentration in the surfactant phase (considerably less than 8%) at θ=∞.

Figure 14B:
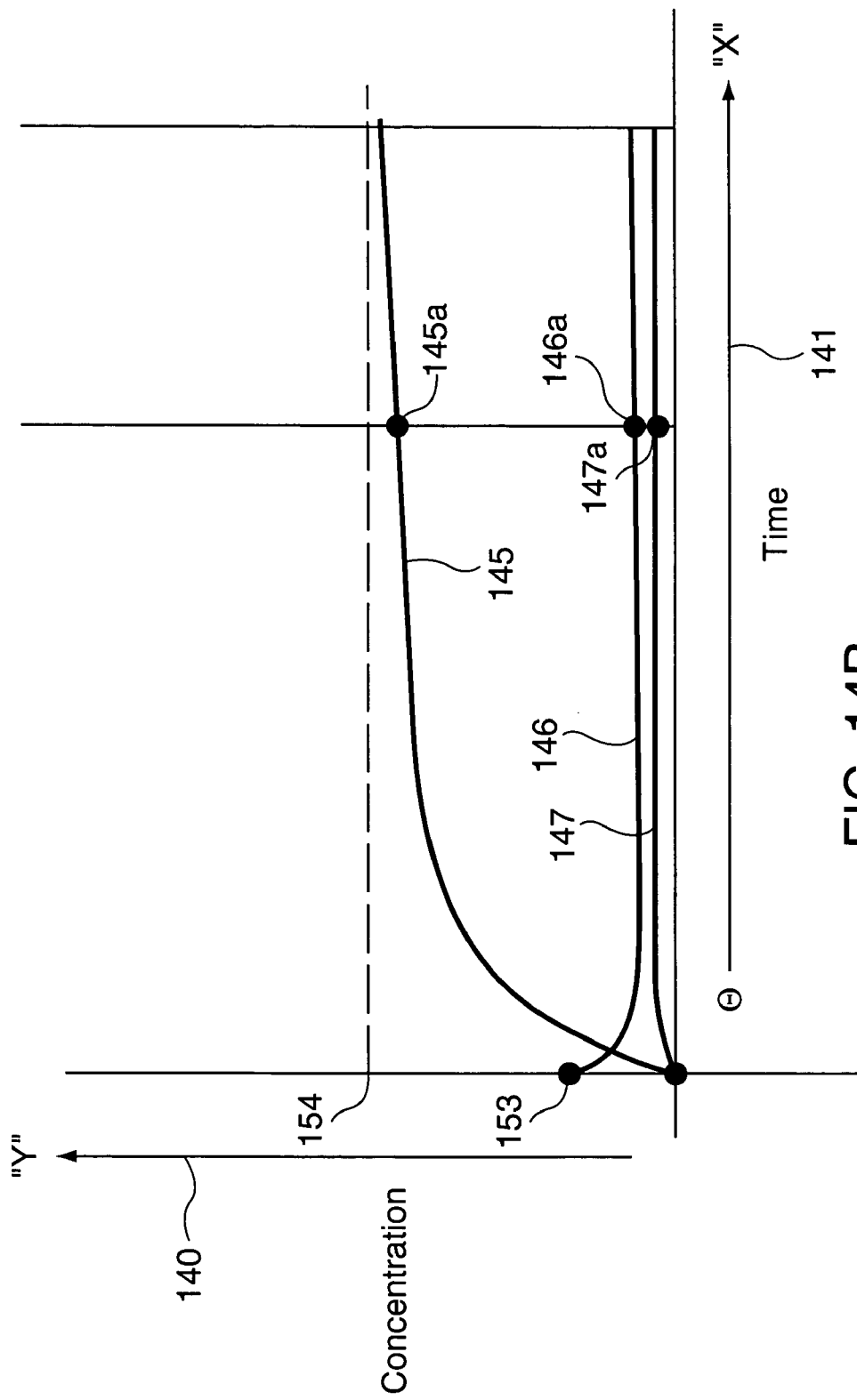
FIG. 14B sets forth for a polymer particle-water-detergent system, graphs of fragrance concentration vs. time (in hours) for polymer particles initially empty (having no fragrance contained in their respective free volumes), for detergent particles initially containing fragrance and for water initially not containing any fragrance. The graph illustrates a 'soak-up' rate for fragrance being absorbed in the polymer particle free volume.

Referring to FIG. 14B, it sets forth for a polymer particle-water-surfactant system, graphs of fragrance concentration (on the "Y" axis, indicated by reference numeral 140) vs. time (in hours) (on the "X" axis, indicated by reference numeral 141) for polymer particles initially empty (having no fragrance contained in their respective free volumes) (the graph being indicated by reference numeral 145, with a data point at about 150 hours being indicated by reference numeral 145a), for surfactant phase (e.g., containing vesicles and/or micelles) initially containing fragrance (the graph being indicated by reference numeral 146 with a data point at 0 hours being indicated by reference numeral 153 and a data point at about 150 hours indicated by reference numeral 146a) and for water initially not containing any fragrance (the graph being indicated by reference numeral 147 with a data point at about 150 hours being indicated by reference numeral 147a). The graph illustrates a 'soak-up' rate for fragrance being absorbed in the polymer particle free volume. Line 154 represents a concentration of about 8%, an asymptote approached by the fragrance concentration in the polymer particle at θ=∞.

All U.S. Patents and Patent Applications described herein are incorporated by reference as if set forth in their entirety.

This invention can be further illustrated by the following examples of preferred embodiments thereof, although it will be understood that these examples are included merely for purposes of illustration and are not intended to limit the scope of the invention, which is only limited by the claims as set forth. Unless noted to the contrary, all percentages are weight percent unless noted to the contrary.

EXAMPLE A

The following fragrance is prepared for use in conjunction with the following Examples 1–6:

| Ingredient | Parts by Weight |
|---|---|
| HEDIONE | 50 |
| LILIAL | 50 |
| γ-methyl ionone | 50 |
| dihydromyrcenol | 50 |
| n-hexyl salicylate | 50 |
| ALDEHYDE AA | 50 |

EXAMPLE I

Two groups of particles of the ethylene-vinyl acetate copolymer, ELVAX described in detail, herein, were milled to (a) an average effective diameter of 150–200 microns (Group A) and (b) an average effective diameter of 10–50 microns (Group B) in liquid nitrogen using the apparatus and technique as described in U.S. Pat. No. 4,731,243. In each of Groups A and B, 300 cc. of the fragrance of Example A was admixed with 100 grams of the milled ethylene-vinyl acetate copolymer, with stirring at 50 rpm, for a period of 12 hours at 28° C. The resulting products were then admixed with the fabric conditioner, DOWNY FREE & SENSITIVE-P(Procter & Gamble Company, Cincinnati, Ohio) to a final fragrance level of 1% and allowed to equilibrate at room temperature for a period of 168 hours. The resulting fabric conditioner compositions were used to wash towels in a standard wash cycle followed by machine drying for one drying cycle at medium/high. The dried towels were evaluated on a scale of 0 to 5 for fragrance intensity (with 5 being the greatest fragrance intensity, and 0 showing no perception of fragrance) and compared to a control that was washed using the same fabric conditioner admixed with the neat fragrance of Example A at a fragrance level of 1%. The towels were aged at room temperature on open shelves and evaluated over a 1 week period. The results are set forth in FIG. 2 described above. FIG. 2 indicates the two fold superiority over the one week period of the use of the 150–200 micron particles of our invention and the 1.5 fold superiority of the 10–50 micron particles of our invention vs. the use of the neat fragrance.

Substantially identical results were achieved when, in place of the particles having the ethylene-vinyl acetate copolymer infrastructure, particles having an infrastructure composed of ETHOCEL Std.45 were used.

EXAMPLE II(A)

Three groups of unfragranced particles having vacant free volumes designated A, B and C of the ethylene-vinyl acetate copolymer, ELVAX described above were milled to an average effective diameter of 150–200 microns in liquid nitrogen using the apparatus and technique as described in U.S. Pat. No. 4,731,243. Similarly, three groups of unfragranced particles, designated D, E and F of the ethylcellulose polymer, ETHOCEL Std.45 described above were milled to an average effective diameter of 150–200 microns in liquid nitrogen using the apparatus and technique as described in U.S. Pat. No. 4,731,243. Similarly, one group of unfragranced particles, designated G of low density polyethylene and one group of unfragranced particles designated H of high density polyethylene were milled to an average effective diameter of 150–200 microns. Groups A, B, D, E, G and H particles were added to an ALL (Lever Brothers Company, Edgewater, N.J.) fabric conditioner formulation which contains fragrance. In addition groups C and F were added to DOWNY fabric conditioner base which contains fragrance. In every case, the amount of fragrance absorbed was quantitated via GC analysis after filtration and solvent extraction of the particles. The ethylene-vinyl acetate copolymer and the ethyl cellulose polymer were ascertained to absorb the fragrance significantly with dependence on the chemical nature of the fragrance molecules as well as the nature of the softener formulation, while particles having an infrastructure composed of low density polyethylene or high density polyethylene absorb indignificant amounts of individual fragrance components. The following table VIII indicates the results on which the foregoing conclusions are based:

TABLE VIII

| Polymer | Fragrance component | ALL Fabric Conditioner | ALL Fabric Conditioner | DOWNY Fabric Conditioner |
|---|---|---|---|---|
| ethylene-vinyl acetate copolymer | | Group A | Group B | Group C |
| ethylene-vinyl acetate copolymer | dihydromyrcenol | 1.7% | 1.5% | 0.1% |
| ethylene-vinyl acetate copolymer | ALDEHYDE AA | 2.2% | 1.6% | 0.2% |
| ethylene-vinyl acetate copolymer | CYCLACET | 5.3% | 5.4% | 0.5% |
| ethylene-vinyl acetate copolymer | LILIAL | 5.1% | 5.4% | 0.4% |
| ethylene-vinyl acetate copolymer | HEDIONE | 4.7% | 4.8% | 0.4% |
| ethylene-vinyl acetate copolymer | TOTAL | 18.9% | 18.7% | 1.6% |
| ethyl cellulose polymer | | Group D | Group E | Group F |
| ethyl cellulose polymer | dihydromyrcenol | 2.9% | 2.0% | 0.4% |
| ethyl cellulose polymer | ALDEHYDE AA | 2.4% | 1.4% | 0.5% |
| ethyl cellulose polymer | CYCLACET | 6.6% | 5.3% | 0.9% |
| ethyl cellulose polymer | LILIAL | 6.3% | 5.6% | 0.6% |
| ethyl cellulose polymer | HEDIONE | 6.0% | 5.4% | 0.9% |
| ethyl cellulose polymer | TOTAL | 24.2% | 19.7% | 3.3% |

TABLE VIII-continued

| Polymer | Fragrance component | ALL Fabric Conditioner | ALL Fabric Conditioner | DOWNY Fabric Conditioner |
|---|---|---|---|---|
| Low Density Polyethylene | | Group G | | |
| Low Density Polyethylene | dihydromyrcenol | 0.1% | | |
| High Density Polyethylene | | Group H | | |
| High Density Polyethylene | ALDEHYDE AA | 0.1% | | |
| High Density Polyethylene | CYCLACET | 0.1% | | |
| High Density Polyethylene | LILIAL | 0.1% | | |
| High Density Polyethylene | HEDIONE | 0.1% | | |

EXAMPLE II(B)

A group of unfragranced particles having vacant free volumes designated J of the ethylene-vinyl acetate copolymer, ELVAX described in detail above were milled to an average effective diameter of 150–200 microns in liquid nitrogen. 100 grams of the particles were added to the 200 milliliters of the fabric conditioner base DOWNY. The resulting mixture was used to wash fabrics in a washing machine. The resulting washed fabric was dried in an automatic dryer. The dried laundry was found to have a significant increase in fragrance intensity vs. a substantially identical batch of fabrics washed and dried using the same fabric conditioner base and an equivalent amount of neat fragrance (prepared according to Example A herein) as opposed to fragrance contained in particle free volumes.

In addition, fabrics which were washed with the particle-containing softener, DOWNY, (containing fragrance) and then line-dried were preferred greater than about 70% of the time, repeatedly by a group of 10 panelists in a double blind study vs. a control which was, DOWNY FREE & SENSITIVE with added neat fragrance (the fragrance of Example A, herein) at the same level, that is 1% weight:weight. Similar results were obtained using other fabric softener products, when the particles of the present invention were utilized compared to the control.

EXAMPLE III

A group of particles designated K of the ethylene-vinyl acetate copolymer, ELVAX described above were milled to an average effective diameter of 150–200 microns in liquid nitrogen using the apparatus and technique described above. A second group of particles, designated L of low density polyethylene were milled to an average effective diameter of 150–200 microns in liquid nitrogen. Each of particle groups K and L, in the amounts of 100 grams was added to separate 200 gram samples of TIDE (Procter & Gamble Company, Cincinnati, Ohio) detergent powder as described in U.S. Pat. Nos. 4,318,818 and 5,916,862 and the resulting mixtures were each placed in a separate jar, after dry-blending of the mixtures. To each jar, in a concentration of 16.7% by weight of the resulting mixture, the Fragrance formulation of Example A was added. Each jar was sealed and shaken. 35 Grams of each of the contents of each jar was then separately added to one liter of water with stirring for a period of 120 seconds, thus enabling the detergent part of each mixture to dissolve, while the polymer particles remained undissolved. The polymer particles were then removed from each mixture by means of filtration and analyzed via solvent extraction followed by gas chromatography of the resulting extracts in order to determine the amount of fragrance absorbed in the free volumes of the respective polymers of Groups K and L. As shown in the bar graphs of FIG. 3, the particles having the infrastructure composed of the ethylene-vinyl acetate copolymer were found to absorb a significant amount (29%) of fragrance from the system, whereas the low density polyethylene absorbed substantially no fragrance.

Accordingly, it is appropriate to conclude that the ethylene-vinyl acetate copolymer particles having an average effective diameter of 150–200 microns can be utilized to soak up compatible fragrance from powder laundry detergent so that when the detergent is used to wash clothing the particles will deposit on the cloth and release a pleasing odor for relatively long periods of time; greater than about a week.

EXAMPLE IV

700 Grams. of unground ethylene-vinyl acetate copolymer pellets having an average effective diameter of 0.5 cm. (ELVAX) were blended with 100 grams. silicon dioxide and 200 grams of the fragrance of Example A. The blending was carried out by placing the ingredients in a 1500 cc. sealed jar and placing the jar on a rotating mixer at 20 revolutions per minute for a period of 12 hours. The resulting pellets, containing soaked-up fragrance, were then fed into a twin barrel extruder with the barrels pre-heated to 150° C., thereby producing a homogeneous molten extrudate. The molten extrudate tow on leaving the extruder was cooled to room temperature and fed into a coarse grinder, and then into a grinder while cooling the particles using liquid nitrogen.

The resulting particles were admixed with TIDE FREE detergent powder (not containing any fragrance) and the resulting mixture was blended in a solids mixer at 35 rpm. The resulting blend was used in a handwash application. Upon addition of the resulting mixture to a bucket of water containing dirty laundry, the detergent dissolved and the remaining particles having infrastructures composed of the ethylene-vinyl acetate copolymer floated to the surface. The exposure of the particles to water altered the thermodynamic balance thereby triggering greater release of fragrance as shown in FIG. 6. After 1 hour, the aroma in the environment proximate the bucket reached a maximum intensity, and then stabilized. The resulting aroma masked the malodour that developed upon soaking and increased the perception of cleanliness and freshness of the wash. Accordingly, it can be properly concluded that the particles having infrastructures composed of the ethylene-vinyl acetate copolymer can be used in laundry handwash to mask the malodour that develops over a period of time when laundry is left to soak for long periods of time, such as greater than 8 hours.

A second experiment was then carried out whereby an ethylcellulose based particle, ETHOCEL Std.45 described above was then substituted for the ethylene-vinyl acetate copolymer particle. In all other respects, the conditions were identical. The ethylcellulose particles were found to release the fragrance 50% faster during the first two hours, thus providing a "burst" effect; and subsequently had a significantly lower (50%) release rate.

A third experiment was then carried out whereby a low density polyethylene (LDPE) particle was then substituted for the ethylene-vinyl acetate copolymer particle. In all other respects, the conditions were identical. The LDPE particles did not release any fragrance and showed no benefit in the application.

EXAMPLE V

Malodour Absorption

A group of particles designated M having infrastructures composed of the ethylene-vinyl acetate copolymer, ELVAX described above were milled to an average effective diameter of 200 microns in liquid. At the rate of 1%, the resulting particles were added to a 10 ppm aqueous isovaleric acid (malodour) solution. After 1 minute, the malodour in the headspace above the solution was significantly reduced vs. the control, which had no particles, but was free isovaleric acid in a concentration of 10 ppm. Using HPLC, it was ascertained that at the rate of 1% the particles having an infrastructure composed of ethylene-vinyl acetate copolymer will absorb 70 parts per million (ppm) isovaleric acid from a solution having a concentration of isovaleric acid of 186 ppm.

EXAMPLE VI

Preparation of Polymethylmethacrylate Particles Containing Substantial Free Volumes 500 Grams. of polymethyl methacrylate unground pellets (ELVACITE 2041 were milled to an average effective diameter of 100 microns in liquid nitrogen. The milled product was divided into ten 50 gram portions designated: A, B, C, D, E, F, G, H, I and J.

At 25° C., portion A is submerged in 300 ml. of the fragrance prepared according to Example A, with stirring a 60 rpm for a period of 10 minutes. No fragrance was absorbed into the particles.

Portion B was heated to 105° C. under a nitrogen atmosphere. Simultaneously, 300 ml. of fragrance prepared according to Example A was heated to 50° C. under 2 atmospheres nitrogen pressure, with stirring at 60 rpm. The heated polymethyl methacrylate particles were then submerged in the fragrance with stirring at 60 rpm, for a period of 10 minutes while maintaining the pressure at 2 atmospheres nitrogen. No fragrance was absorbed into the particles.

Portions C, D, E and F were separately admixed, each with 50 cc. of, respectively, 95%, 75%, 50%, and 25% aqueous ethanol, and each of the resultant slurries was stirred at 25° C. at 60 rpm for a period of 60 seconds. In each case, particles were separated from the aqueous ethanol by means of filtration. Each of the resulting particle groups was then submerged, with stirring at 60 rpm in 300 ml. fragrance prepared according to Example A for a period of 60 seconds. In each case the particles absorbed fragrance to 45% by weight of the final particle.

Portions G, H, I and J were separately admixed, each with 50 cc. of, respectively, 95%, 75%, 50%, and 25% aqueous ethanol, and each of the resultant slurries was stirred at 25° C. at 60 rpm for a period of 60 seconds. In each case, particles were separated from the aqueous ethanol by means of filtration. Each of the resulting particle groups was then submerged, with stirring at 60 rpm in 300 ml. fragrance prepared according to Example A for period of 300 seconds. In each case the particles absorbed fragrance to 50% by weight of the final particle.

What is claimed is:

1. A process for imparting an aesthetically-pleasing substantive fragrance to and/or substantially eliminating a perceived malodour from aqueous surfactant-containing composition-treated fabrics, hair follicles, mammalian epidermis or solid surfaces during treatment of said fabrics, hair follicles, mammalian epidermis or solid surfaces with surfactant-containing compositions comprising the steps of:
   i. providing a plurality of polymer particles (a) having a volume average diameter of from about 0.01 microns to about 1000 microns, (b) having a solid or viscoelastic infrastructure which is composed of a substance selected from the group consisting of an ethylene-vinyl acetate copolymer containing from about 10% to about 90% vinyl acetate monomeric units, said polymers having a number average molecular weight of from about 8000 to about $1 \times 10^6$ and (c) having a substantially solid or viscoelastic three-dimensional porous infrastructure having an internal free volume containing a liquid phase fragrance material removably entrapped in said infrastructure, contained in the interstices of said infrastructure and outwardly transportable from said infrastructure, each of the components of which fragrance material having a C $\log_{10}$ P in the range of from about 1 to about 7, the initial weight % of fragrance material contained in said plurality of polymer particles being from about 0.5% to about 50% by weight of the plurality of polymer particles, each of said fragrance components being compatible with said polymer; wherein the plurality of polymer particles is produced by a process comprising the sequential steps of (a) blending polymer pellets with fragrance material for a period of time of from about 0.05 hours to about 20 hours; (b) extruding the resulting product at a temperature of from about 130° C. to about 170° C. to form an extrudate; (c) cooling the resulting extrudate to a temperature in the range of from about 15° C. to about 40° C. and (d) cryogrinding the resulting extrudate to form cryoground particles;
   ii. providing a fabric, hair follicle, mammalian epidermis or solid surface treatment quantity of an aqueous composition comprising from about 1% to about 25% by weight of at least one surfactant which aqueous composition is designed to be in intimate treatment contact with, in the alternative, (a) at least one fabric article over a fabric treatment period of time in a fabric treatment concentration and temperature; or (b) at least one solid surface over a solid surface treatment period of time in a solid surface treatment concentration and temperature; or (c) at least one hair follicle over a hair follicle treatment period of time in a hair follicle treatment concentration and temperature or (d) a mammalian epidermis surface over a mammalian epidermis surface treatment period of time in a mammalian epidermis surface treatment concentration and temperature;
   iii. providing treatment means for enabling treatment of said fabrics, said hair follicles, said mammalian epidermis or said solid surfaces;
   iv. introducing (a) said aqueous composition; (b) said at least one fabric article, said at least one hair follicle, said at least one mammalian epidermis or said at least one solid surface; and (c) said plurality of polymer particles into said treatment means;
   v. engaging said treatment means for a treatment period of time at a treatment temperature;
   vi. disengaging said treatment means;
   vii. removing (a) said at least one fabric article or (b) said at least one solid surface or (c) said hair follicles or (d) said mammalian epidermis surface from said treatment means;
   viii. rinsing (a) said at least one fabric article or (b) said at least one solid surface or (c) said hair follicles or (d) said mammalian epidermis surface; and
   ix. drying (a) said at least one fabric article or (b) said at least one solid surface or (c) said hair follicles or (d) said mammalian epidermis surface
wherein fragrance components and malodour molecules are compatible with said polymers.

2. The process of claim 1 wherein the plurality of polymer particles is produced by a process comprising the sequential steps of (a) blending polymer pellets with silicon dioxide and fragrance material for a period of time of from about 0.05 hours to about 20 hours; (b) extruding the resulting product at a temperature of from about 130° C. to about 170° C. to form an extrudate; (c) cooling the resulting extrudate to a temperature in the range of from about 15° C. to about 40° C. and (d) cryogrinding the resulting extrudate to form cryoground particles.

3. The process of claim 1 wherein the plurality of polymer particles is produced by a process comprising the sequential steps of (a) extruding polymer pellets with one or more foam forming agents to from a foamed extrudate; (b) cooling the resulting extrudate to form an extrudate tow; (c) particularizing the resulting tow to form microporous polymer particles; and (d) admixing the resulting particles with a fragrance composition, the components of which are compatible with the polymer.

* * * * *